US012788573B2

(12) United States Patent
Strohkirch et al.

(10) Patent No.: US 12,788,573 B2
(45) Date of Patent: Nov. 10, 2026

(54) IMPLANT PEG WITH MULTIPLE COMPONENTS

(71) Applicant: WRIGHT MEDICAL TECHNOLOGY, INC., Memphis, TN (US)

(72) Inventors: Terrance W. Strohkirch, Memphis, TN (US); Ramon Luna, Arlington, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 756 days.

(21) Appl. No.: 18/254,394

(22) PCT Filed: Jan. 11, 2022

(86) PCT No.: PCT/US2022/070130

§ 371 (c)(1),
(2) Date: May 25, 2023

(87) PCT Pub. No.: WO2022/183150

PCT Pub. Date: Sep. 1, 2022

(65) Prior Publication Data

US 2024/0024120 A1 Jan. 25, 2024

Related U.S. Application Data

(60) Provisional application No. 63/153,040, filed on Feb. 24, 2021.

(51) Int. Cl.
*A61F 2/42* (2006.01)
*A61F 2/30* (2006.01)

(52) U.S. Cl.
CPC ........ *A61F 2/4202* (2013.01); *A61F 2/30749* (2013.01); *A61F 2/30771* (2013.01);
(Continued)

(58) Field of Classification Search
CPC ................ A61F 2/4202; A61F 2/30749; A61F 2/30771; A61F 2002/30604;
(Continued)

(56) References Cited

U.S. PATENT DOCUMENTS

| | | |
|---|---|---|
| 3,314,420 A | 4/1967 | Smith et al. |
| 3,605,123 A | 9/1971 | Hahn |

(Continued)

FOREIGN PATENT DOCUMENTS

| | | |
|---|---|---|
| CN | 1662186 | 8/2005 |
| CN | 101111197 | 1/2008 |

(Continued)

OTHER PUBLICATIONS

International Preliminary Report on Patentability issued in connection with International Patent Application No. PCT/US2022/070130, Sep. 7, 2023, 13 pages.

(Continued)

*Primary Examiner* — Suzette J Gherbi
(74) *Attorney, Agent, or Firm* — DUANE MORRIS LLP

(57) ABSTRACT

Provided is a tibial tray component in an ankle replacement prosthetic system that comprises modular fixation elements that provide surgeons with variety of interchangeable fixation options. Also provided is a tapered peg that provides enhanced bone plate fixation.

20 Claims, 30 Drawing Sheets

(52) U.S. Cl.
CPC ............... *A61F 2002/30604* (2013.01); *A61F 2002/30774* (2013.01); *A61F 2002/30787* (2013.01); *A61F 2002/30841* (2013.01); *A61F 2002/30878* (2013.01); *A61F 2002/30894* (2013.01); *A61F 2002/4205* (2013.01); *A61F 2002/4207* (2013.01)

(58) Field of Classification Search
CPC .... A61F 2002/30878; A61F 2002/4205; A61F 2002/30332; A61F 2002/30607
See application file for complete search history.

(56) References Cited

U.S. PATENT DOCUMENTS 3,798,679 A 3/1974 Ewald
3,808,606 A 5/1974 Tronzo
3,843,975 A 10/1974 Tronzo
3,855,638 A 12/1974 Pilliar
3,938,198 A 2/1976 Kahn et al.
3,987,499 A 10/1976 Scharbach et al.
4,052,753 A 10/1977 Dedo
4,055,862 A 11/1977 Farling
4,085,466 A 4/1978 Goodfellow et al.
4,098,626 A 7/1978 Graham et al.
4,203,444 A 5/1980 Bonnell et al.
4,213,816 A 7/1980 Morris
4,340,978 A 7/1982 Buechel et al.
4,368,040 A 1/1983 Weissman
4,436,684 A 3/1984 White
4,501,266 A 2/1985 McDaniel
4,502,161 A 3/1985 Wall
4,586,496 A 5/1986 Keller
4,594,380 A 6/1986 Chapin et al.
4,601,290 A 7/1986 Effron et al.
4,609,551 A 9/1986 Caplan et al.
4,627,853 A 12/1986 Campbell et al.
4,703,751 A 11/1987 Pohl
4,704,686 A 11/1987 Aldinger
4,715,860 A 12/1987 Amstutz et al.
4,721,104 A 1/1988 Kaufman et al.
4,759,350 A 7/1988 Dunn et al.
4,769,040 A 9/1988 Wevers
4,841,975 A 6/1989 Woolson
4,846,835 A 7/1989 Grande
4,865,607 A 9/1989 Witzel et al.
4,880,429 A 11/1989 Stone
4,936,862 A 6/1990 Walker et al.
4,979,949 A 12/1990 Matsen, III et al.
5,002,547 A 3/1991 Poggie
5,041,138 A 8/1991 Vacanti et al.
5,059,216 A 10/1991 Winters
5,067,964 A 11/1991 Richmond et al.
5,122,144 A 6/1992 Bert et al.
5,129,908 A 7/1992 Petersen
5,133,759 A 7/1992 Turner
5,154,717 A 10/1992 Matsen, III et al.
5,162,430 A 11/1992 Rhee et al.
5,171,322 A 12/1992 Kenny
5,197,985 A 3/1993 Caplan et al.
5,206,023 A 4/1993 Hunziker
5,226,914 A 7/1993 Caplan et al.
5,234,433 A 8/1993 Bert et al.
5,250,050 A 10/1993 Poggie et al.
5,258,032 A 11/1993 Bertin
5,270,300 A 12/1993 Hunziker
5,288,797 A 2/1994 Khalil et al.
5,303,148 A 4/1994 Mattson et al.
5,306,311 A 4/1994 Stone et al.
5,314,482 A 5/1994 Goodfellow et al.
5,344,459 A 9/1994 Swartz
5,360,446 A 11/1994 Kennedy
5,365,996 A 11/1994 Crook
5,368,858 A 11/1994 Hunziker
5,370,692 A 12/1994 Fink et al.
5,380,332 A 1/1995 Ferrante
5,387,216 A 2/1995 Thornhill et al.
5,454,816 A 10/1995 Ashby
5,462,550 A 10/1995 Dietz et al.
5,468,787 A 11/1995 Braden et al.
5,474,559 A 12/1995 Bertin et al.
5,478,739 A 12/1995 Slivka et al.
5,486,180 A 1/1996 Dietz et al.
5,501,687 A 3/1996 Willert et al.
5,503,162 A 4/1996 Athanasiou et al.
5,520,695 A 5/1996 Luckman
5,523,843 A 6/1996 Yamane et al.
5,540,696 A 7/1996 Booth, Jr. et al.
5,542,947 A 8/1996 Treacy
5,554,190 A 9/1996 Draenert
5,556,432 A 9/1996 Kubein-Meesenburg et al.
5,571,205 A 11/1996 James
5,575,793 A 11/1996 Carls et al.
5,578,037 A 11/1996 Sanders et al.
5,593,450 A 1/1997 Scott et al.
5,597,379 A 1/1997 Haines et al.
5,601,563 A 2/1997 Burke et al.
5,613,970 A 3/1997 Houston et al.
5,616,146 A 4/1997 Murray
5,630,820 A 5/1997 Todd
5,632,745 A 5/1997 Schwartz
5,649,929 A 7/1997 Callaway
5,658,290 A 8/1997 Techeira
5,671,741 A 9/1997 Lang et al.
5,682,886 A 11/1997 Delp et al.
5,683,466 A 11/1997 Vitale
5,684,562 A 11/1997 Fujieda
5,688,282 A 11/1997 Baron et al.
5,728,162 A 3/1998 Eckhoff
5,735,277 A 4/1998 Schuster
5,749,874 A 5/1998 Schwartz
5,749,876 A 5/1998 Duvillier et al.
5,765,561 A 6/1998 Chen et al.
5,768,134 A 6/1998 Swaelens et al.
5,769,899 A 6/1998 Schwartz et al.
5,786,217 A 7/1998 Tuba et al.
5,798,924 A 8/1998 Eufinger et al.
5,800,438 A 9/1998 Tuke et al.
5,824,083 A 10/1998 Draenert
5,827,289 A 10/1998 Reiley et al.
5,830,216 A 11/1998 Insall et al.
5,835,619 A 11/1998 Morimoto et al.
5,842,477 A 12/1998 Naughton et al.
5,847,804 A 12/1998 Sarver et al.
5,853,746 A 12/1998 Hunziker
5,860,981 A 1/1999 Bertin et al.
5,871,018 A 2/1999 Delp et al.
5,871,542 A 2/1999 Goodfellow et al.
5,871,546 A 2/1999 Colleran et al.
5,879,390 A 3/1999 Kubein-Meesenburg et al.
5,880,976 A 3/1999 DiGioia, III et al.
5,885,296 A 3/1999 Masini
5,885,297 A 3/1999 Matsen, III
5,885,298 A 3/1999 Herrington et al.
5,897,559 A 4/1999 Masini
5,899,859 A 5/1999 Votruba et al.
5,900,245 A 5/1999 Sawhney et al.
5,906,934 A 5/1999 Grande et al.
5,911,723 A 6/1999 Ashby et al.
5,916,220 A 6/1999 Masini
5,939,323 A 8/1999 Valentini et al.
5,951,475 A 9/1999 Gueziec et al.
5,961,523 A 10/1999 Masini
5,968,051 A 10/1999 Luckman et al.
5,972,385 A 10/1999 Liu et al.
5,995,738 A 11/1999 DiGioia, III et al.
6,001,895 A 12/1999 Harvey et al.
6,002,859 A 12/1999 DiGioia, III et al.
6,006,126 A 12/1999 Cosman
6,007,537 A 12/1999 Burkinshaw et al.
6,010,509 A 1/2000 Delgado et al.
6,013,081 A 1/2000 Burkinshaw et al.
6,013,103 A 1/2000 Kaufman et al.
6,046,379 A 4/2000 Stone et al.

(56) References Cited

U.S. PATENT DOCUMENTS

| | | | |
|---|---|---|---|
| 6,056,754 | A | 5/2000 | Haines et al. |
| 6,056,756 | A | 5/2000 | Eng et al. |
| 6,057,927 | A | 5/2000 | Levesque et al. |
| 6,077,270 | A | 6/2000 | Katz |
| 6,082,364 | A | 7/2000 | Balian et al. |
| 6,090,144 | A | 7/2000 | Letot et al. |
| 6,093,204 | A | 7/2000 | Stone |
| 6,096,043 | A | 8/2000 | Techiera et al. |
| 6,102,916 | A | 8/2000 | Masini |
| 6,106,529 | A | 8/2000 | Techiera |
| 6,110,209 | A | 8/2000 | Stone |
| 6,120,541 | A | 9/2000 | Johnson |
| 6,126,690 | A | 10/2000 | Ateshian et al. |
| 6,139,578 | A | 10/2000 | Lee et al. |
| 6,156,069 | A | 12/2000 | Amstutz |
| 6,161,080 | A | 12/2000 | Aouni-Ateshian et al. |
| 6,187,010 | B1 | 2/2001 | Masini |
| 6,200,606 | B1 | 3/2001 | Peterson et al. |
| 6,203,546 | B1 | 3/2001 | MacMahon |
| 6,203,576 | B1 | 3/2001 | Afriat et al. |
| 6,205,411 | B1 | 3/2001 | DiGioia, III et al. |
| 6,206,927 | B1 | 3/2001 | Fell et al. |
| 6,214,369 | B1 | 4/2001 | Grande et al. |
| 6,217,894 | B1 | 4/2001 | Sawhney et al. |
| 6,219,571 | B1 | 4/2001 | Hargreaves et al. |
| 6,224,632 | B1 | 5/2001 | Pappas et al. |
| 6,235,060 | B1 | 5/2001 | Kubein-Meesenburg et al. |
| 6,251,143 | B1 | 6/2001 | Schwartz et al. |
| 6,254,639 | B1 | 7/2001 | Peckitt |
| 6,277,151 | B1 | 8/2001 | Lee et al. |
| 6,281,195 | B1 | 8/2001 | Rueger et al. |
| 6,283,980 | B1 | 9/2001 | Vibe-Hansen et al. |
| 6,296,646 | B1 | 10/2001 | Williamson |
| 6,299,905 | B1 | 10/2001 | Peterson et al. |
| 6,322,588 | B1 | 11/2001 | Ogle et al. |
| 6,327,491 | B1 | 12/2001 | Franklin et al. |
| 6,328,765 | B1 | 12/2001 | Hardwick et al. |
| 6,344,043 | B1 | 2/2002 | Pappas |
| 6,344,059 | B1 | 2/2002 | Krakovits et al. |
| 6,352,558 | B1 | 3/2002 | Spector |
| 6,358,253 | B1 | 3/2002 | Torrie et al. |
| 6,365,405 | B1 | 4/2002 | Salzmann et al. |
| 6,371,958 | B1 | 4/2002 | Overaker |
| 6,373,250 | B1 | 4/2002 | Tsoref et al. |
| 6,375,658 | B1 | 4/2002 | Hangody et al. |
| 6,379,367 | B1 | 4/2002 | Vibe-Hansen et al. |
| 6,382,028 | B1 | 5/2002 | Wooh et al. |
| 6,383,228 | B1 | 5/2002 | Schmotzer |
| 6,387,131 | B1 | 5/2002 | Miehlke et al. |
| 6,409,767 | B1 * | 6/2002 | Perice .................. A61F 2/4202 623/21.18 |
| 6,429,013 | B1 | 8/2002 | Halvorsen et al. |
| 6,443,988 | B2 | 9/2002 | Felt et al. |
| 6,443,991 | B1 | 9/2002 | Running |
| 6,444,222 | B1 | 9/2002 | Asculai et al. |
| 6,459,927 | B1 | 10/2002 | Franklin et al. |
| 6,459,948 | B1 | 10/2002 | Ateshian et al. |
| 6,468,314 | B2 | 10/2002 | Schwartz et al. |
| 6,478,799 | B1 | 11/2002 | Williamson |
| 6,479,996 | B1 | 11/2002 | Hoogeveen et al. |
| 6,510,334 | B1 | 1/2003 | Schuster et al. |
| 6,520,964 | B2 | 2/2003 | Tallarida et al. |
| 6,558,421 | B1 | 5/2003 | Fell et al. |
| 6,560,476 | B1 | 5/2003 | Pelletier et al. |
| 6,575,980 | B1 | 6/2003 | Robie et al. |
| 6,620,168 | B1 | 9/2003 | Lombardo et al. |
| 6,626,945 | B2 | 9/2003 | Simon et al. |
| 6,626,948 | B2 | 9/2003 | Storer et al. |
| 6,632,225 | B2 | 10/2003 | Sanford et al. |
| 6,632,235 | B2 | 10/2003 | Weikel et al. |
| 6,652,587 | B2 | 11/2003 | Felt et al. |
| 6,673,077 | B1 | 1/2004 | Katz |
| 6,679,917 | B2 | 1/2004 | Ek |
| 6,712,856 | B1 | 3/2004 | Carignan et al. |
| 6,738,657 | B1 | 5/2004 | Franklin et al. |
| 6,905,514 | B2 | 6/2005 | Carignan et al. |
| 6,916,341 | B2 | 7/2005 | Rolston |
| 6,928,742 | B2 | 8/2005 | Broers et al. |
| 6,932,842 | B1 | 8/2005 | Litschko et al. |
| 6,942,667 | B1 | 9/2005 | Song |
| 6,944,518 | B2 | 9/2005 | Roose |
| 6,969,393 | B2 | 11/2005 | Pinczewski et al. |
| 6,980,849 | B2 | 12/2005 | Sasso |
| 6,988,015 | B1 | 1/2006 | Schopf et al. |
| 6,993,374 | B2 | 1/2006 | Sasso |
| 7,008,430 | B2 | 3/2006 | Dong et al. |
| 7,058,439 | B2 | 6/2006 | Eaton et al. |
| 7,060,074 | B2 | 6/2006 | Rosa et al. |
| 7,104,997 | B2 | 9/2006 | Lionberger et al. |
| 7,115,131 | B2 | 10/2006 | Engh et al. |
| 7,117,027 | B2 | 10/2006 | Zheng et al. |
| 7,141,053 | B2 | 11/2006 | Rosa et al. |
| 7,184,814 | B2 | 2/2007 | Lang et al. |
| 7,201,762 | B2 | 4/2007 | Green, Jr. et al. |
| 7,217,276 | B2 | 5/2007 | Henderson et al. |
| 7,239,908 | B1 | 7/2007 | Alexander et al. |
| 7,245,697 | B2 | 7/2007 | Lang |
| 7,282,054 | B2 | 10/2007 | Steffensmeier et al. |
| 7,292,674 | B2 | 11/2007 | Lang |
| 7,347,690 | B2 | 3/2008 | Jordan et al. |
| 7,364,581 | B2 | 4/2008 | Michalowicz |
| 7,377,924 | B2 | 5/2008 | Raistrick et al. |
| 7,379,529 | B2 | 5/2008 | Lang |
| 7,467,892 | B2 | 12/2008 | Lang et al. |
| 7,468,075 | B2 | 12/2008 | Lang et al. |
| 7,534,246 | B2 | 5/2009 | Reiley et al. |
| 7,534,263 | B2 | 5/2009 | Burdulis, Jr. et al. |
| 7,618,451 | B2 | 11/2009 | Berez et al. |
| 7,747,305 | B2 | 6/2010 | Dean et al. |
| 7,806,896 | B1 | 10/2010 | Bonutti |
| 7,881,768 | B2 | 2/2011 | Lang et al. |
| 7,981,158 | B2 | 7/2011 | Fitz et al. |
| 7,983,777 | B2 | 7/2011 | Melton et al. |
| 8,036,729 | B2 | 10/2011 | Lang et al. |
| 8,062,302 | B2 | 11/2011 | Lang et al. |
| 8,066,708 | B2 | 11/2011 | Lang et al. |
| 8,083,745 | B2 | 12/2011 | Lang et al. |
| 8,105,330 | B2 | 1/2012 | Fitz et al. |
| 8,112,142 | B2 | 2/2012 | Alexander et al. |
| 8,122,592 | B2 | 2/2012 | Burdulis, Jr. et al. |
| RE43,282 | E | 3/2012 | Alexander et al. |
| 8,496,663 | B2 | 7/2013 | White et al. |
| 8,535,319 | B2 | 9/2013 | Ball |
| 8,715,362 | B2 | 5/2014 | Reiley et al. |
| 8,808,297 | B2 | 8/2014 | Stemniski |
| 8,808,303 | B2 | 8/2014 | Stemniski |
| 9,005,255 | B2 | 4/2015 | Lewis et al. |
| 9,017,334 | B2 | 4/2015 | Carroll et al. |
| 9,125,674 | B2 | 9/2015 | White et al. |
| 9,265,511 | B2 | 2/2016 | White et al. |
| 9,402,640 | B2 | 8/2016 | Stemniski et al. |
| 10,105,168 | B2 | 10/2018 | Blau |
| 10,130,430 | B2 | 11/2018 | Kao et al. |
| 10,390,842 | B2 | 8/2019 | Sander |
| 10,413,308 | B2 | 9/2019 | Stemniski et al. |
| 10,456,179 | B2 | 10/2019 | Luna et al. |
| 10,667,867 | B2 | 6/2020 | Ashish et al. |
| 10,835,265 | B2 | 11/2020 | White et al. |
| 10,835,266 | B2 | 11/2020 | White et al. |
| 11,147,627 | B2 | 10/2021 | Gangwar et al. |
| 11,172,945 | B1 | 11/2021 | Lian |
| 2001/0001120 | A1 | 5/2001 | Masini |
| 2001/0010023 | A1 | 7/2001 | Schwartz et al. |
| 2001/0039455 | A1 | 11/2001 | Simon et al. |
| 2002/0013626 | A1 | 1/2002 | Geisllich et al. |
| 2002/0029038 | A1 | 3/2002 | Haines |
| 2002/0045940 | A1 | 4/2002 | Giannelli et al. |
| 2002/0059049 | A1 | 5/2002 | Bradbury et al. |
| 2002/0068979 | A1 | 6/2002 | Brown et al. |
| 2002/0072821 | A1 | 6/2002 | Baker |
| 2002/0079601 | A1 | 6/2002 | Russell et al. |
| 2002/0082703 | A1 | 6/2002 | Repicci |
| 2002/0087274 | A1 | 7/2002 | Alexander et al. |
| 2002/0106625 | A1 | 8/2002 | Hung et al. |

(56) References Cited

U.S. PATENT DOCUMENTS

2002/0115647 A1 8/2002 Halvorsen et al.
2002/0120274 A1 8/2002 Overaker et al.
2002/0120281 A1 8/2002 Overaker
2002/0123817 A1 9/2002 Clasbrummel et al.
2002/0127264 A1 9/2002 Felt et al.
2002/0133230 A1 9/2002 Repicci
2002/0143402 A1 10/2002 Steinberg
2002/0151986 A1 10/2002 Asculai et al.
2002/0156150 A1 10/2002 Asculai et al.
2002/0156479 A1 10/2002 Schulzki et al.
2002/0173852 A1 11/2002 Felt et al.
2002/0183850 A1 12/2002 Felt et al.
2002/0198531 A1 12/2002 Millard et al.
2003/0028196 A1 2/2003 Bonutti
2003/0055500 A1 3/2003 Fell et al.
2003/0055501 A1 3/2003 Fell et al.
2003/0055502 A1 3/2003 Lang et al.
2003/0060882 A1 3/2003 Fell et al.
2003/0060883 A1 3/2003 Fell et al.
2003/0060884 A1 3/2003 Fell et al.
2003/0060885 A1 3/2003 Fell et al.
2003/0100907 A1 5/2003 Rosa et al.
2003/0100953 A1 5/2003 Rosa et al.
2003/0120347 A1 6/2003 Steinberg
2003/0158558 A1 8/2003 Horn
2003/0158606 A1 8/2003 Coon et al.
2003/0163137 A1 8/2003 Smucker et al.
2003/0173695 A1 9/2003 Monkhouse et al.
2003/0216669 A1 11/2003 Lang et al.
2003/0225457 A1 12/2003 Justin et al.
2003/0236521 A1 12/2003 Brown et al.
2003/0236526 A1 12/2003 Van Hoeck et al.
2004/0098133 A1 5/2004 Carignan et al.
2004/0102852 A1 5/2004 Johnson et al.
2004/0122521 A1 6/2004 Lee et al.
2004/0133276 A1 7/2004 Lang et al.
2004/0138754 A1 7/2004 Lang et al.
2004/0147927 A1 7/2004 Tsougarakis et al.
2004/0153079 A1 8/2004 Tsougarakis et al.
2004/0153162 A1 8/2004 Sanford et al.
2004/0153164 A1 8/2004 Sanford et al.
2004/0167390 A1 8/2004 Alexander et al.
2004/0167630 A1 8/2004 Rolston
2004/0193280 A1 9/2004 Webster et al.
2004/0199166 A1 10/2004 Schmieding et al.
2004/0204644 A1 10/2004 Tsougarakis et al.
2004/0204760 A1 10/2004 Fitz et al.
2004/0236424 A1 11/2004 Berez et al.
2004/0249386 A1 12/2004 Faoro
2005/0015153 A1 1/2005 Goble et al.
2005/0021039 A1 1/2005 Cusick et al.
2005/0043807 A1 2/2005 Wood
2005/0049603 A1 3/2005 Calton et al.
2005/0055028 A1 3/2005 Haines
2005/0085920 A1 4/2005 Williamson
2005/0107883 A1 5/2005 Goodfried et al.
2005/0107884 A1 5/2005 Johnson et al.
2005/0119664 A1 6/2005 Carignan et al.
2005/0143745 A1 6/2005 Hodorek et al.
2005/0148843 A1 7/2005 Roose
2005/0171545 A1 8/2005 Walsh et al.
2005/0171612 A1 8/2005 Rolston
2005/0187555 A1 8/2005 Biedermann et al.
2005/0192588 A1 9/2005 Garcia
2005/0216305 A1 9/2005 Funderud
2005/0234461 A1 10/2005 Burdulis, Jr. et al.
2005/0267584 A1 12/2005 Burdulis et al.
2006/0052795 A1 3/2006 Burdulis et al.
2006/0111722 A1 5/2006 Bouadi
2006/0149283 A1 7/2006 May et al.
2006/0200162 A1 9/2006 Farling et al.
2006/0235421 A1 10/2006 Rosa et al.
2007/0015995 A1 1/2007 Lang
2007/0073305 A1 3/2007 Lionberger et al.
2007/0118141 A1 5/2007 Marchyn et al.
2007/0162025 A1 7/2007 Tornier et al.
2007/0198022 A1 8/2007 Lang et al.
2007/0203430 A1 8/2007 Lang et al.
2007/0233128 A1 10/2007 Schmieding et al.
2007/0233151 A1 10/2007 Chudik
2007/0233156 A1 10/2007 Metzger
2007/0276224 A1 11/2007 Lang et al.
2007/0293868 A1 12/2007 Delfosse et al.
2008/0004709 A1 1/2008 O'Neill et al.
2008/0015433 A1 1/2008 Alexander et al.
2008/0025463 A1 1/2008 Lang et al.
2008/0031412 A1 2/2008 Delfosse et al.
2008/0058613 A1 3/2008 Lang et al.
2008/0058945 A1 3/2008 Hajaj et al.
2008/0114370 A1 5/2008 Schoenefeld
2008/0170659 A1 7/2008 Lang et al.
2008/0195109 A1 8/2008 Hunter et al.
2008/0195216 A1 8/2008 Lang
2008/0219412 A1 9/2008 Lang
2008/0243127 A1 10/2008 Lang
2008/0255565 A1 10/2008 Fletcher
2008/0275452 A1 11/2008 Lang et al.
2008/0281328 A1 11/2008 Lang et al.
2008/0281329 A1 11/2008 Lang et al.
2008/0281426 A1 11/2008 Fitz et al.
2008/0287953 A1 11/2008 Sers
2009/0024131 A1 1/2009 Metzger et al.
2009/0043310 A1 2/2009 Rasmussen
2009/0076371 A1 3/2009 Lang et al.
2009/0087276 A1 4/2009 Rose
2009/0088753 A1 4/2009 Aram et al.
2009/0088758 A1 4/2009 Bennett
2009/0099567 A1 4/2009 Zajac
2009/0131941 A1 5/2009 Park et al.
2009/0131942 A1 5/2009 Aker et al.
2009/0149964 A1 6/2009 May et al.
2009/0198244 A1 8/2009 Leibel
2009/0204115 A1 8/2009 Dees et al.
2009/0222014 A1 9/2009 Bojarski et al.
2009/0307893 A1 12/2009 Bojarski et al.
2010/0057133 A1 3/2010 Simon
2010/0076441 A1 3/2010 May et al.
2010/0160917 A1 6/2010 Fitz et al.
2010/0262150 A1 10/2010 Lian
2010/0274251 A1 10/2010 Ranft
2010/0281678 A1 11/2010 Burdulis, Jr. et al.
2010/0298894 A1 11/2010 Bojarski et al.
2010/0305573 A1 12/2010 Fitz et al.
2010/0305574 A1 12/2010 Fitz et al.
2011/0066193 A1 3/2011 Lang et al.
2011/0071581 A1 3/2011 Lang et al.
2011/0213368 A1 9/2011 Fitz et al.
2011/0213373 A1 9/2011 Fitz et al.
2011/0213374 A1 9/2011 Fitz et al.
2011/0213377 A1 9/2011 Lang et al.
2011/0213427 A1 9/2011 Fitz et al.
2011/0213428 A1 9/2011 Fitz et al.
2011/0213429 A1 9/2011 Lang et al.
2011/0213430 A1 9/2011 Lang et al.
2011/0213431 A1 9/2011 Fitz et al.
2011/0218539 A1 9/2011 Fitz et al.
2011/0218542 A1 9/2011 Lian et al.
2011/0218584 A1 9/2011 Fitz et al.
2011/0230888 A1 9/2011 Lang et al.
2011/0238073 A1 9/2011 Lang et al.
2011/0313423 A1 12/2011 Lang et al.
2011/0319897 A1 12/2011 Lang et al.
2011/0319900 A1 12/2011 Lang et al.
2012/0029520 A1 2/2012 Lang et al.
2012/0041446 A1 2/2012 Wong et al.
2012/0066892 A1 3/2012 Lang et al.
2012/0071881 A1 3/2012 Lang et al.
2012/0071882 A1 3/2012 Lang et al.
2012/0071883 A1 3/2012 Lang et al.
2012/0072185 A1 3/2012 Lang et al.
2012/0101503 A1 4/2012 Lang et al.
2012/0143197 A1 6/2012 Lang et al.
2012/0151730 A1 6/2012 Fitz et al.
2012/0158001 A1 6/2012 Burdulis, Jr. et al.

(56) References Cited

U.S. PATENT DOCUMENTS

| | | | |
|---|---|---|---|
| 2013/0261628 A1 | 10/2013 | Burley et al. | |
| 2014/0270065 A1 | 9/2014 | Aram et al. | |
| 2014/0276853 A1 | 9/2014 | Long et al. | |
| 2015/0320567 A1 | 11/2015 | Terrill et al. | |
| 2016/0262903 A1 | 9/2016 | West | |
| 2018/0055648 A1* | 3/2018 | Dhillon | A61F 2/4202 |
| 2018/0303490 A1 | 10/2018 | Loring et al. | |
| 2019/0070012 A1* | 3/2019 | Leemrijse | A61F 2/30749 |
| 2020/0015867 A1 | 1/2020 | Luna et al. | |
| 2020/0113712 A1* | 4/2020 | Luna | A61B 17/1682 |
| 2020/0330238 A1* | 10/2020 | Calamel | A61F 2/4202 |
| 2020/0337850 A1 | 10/2020 | Reiley | |
| 2021/0378753 A1 | 12/2021 | Christen et al. | |

FOREIGN PATENT DOCUMENTS

| | | |
|---|---|---|
| DE | 2306552 | 8/1974 |
| DE | 3516743 | 11/1986 |
| DE | 44 34 539 | 4/1996 |
| DE | 20303498 | 8/2003 |
| DE | 202008017199 | 3/2009 |
| DE | 202008017200 | 3/2009 |
| EP | 0377901 | 10/1989 |
| EP | 0528080 | 2/1993 |
| EP | 0530804 | 10/1993 |
| EP | 0626156 | 11/1994 |
| EP | 0704193 | 4/1996 |
| EP | 0896825 | 2/1999 |
| EP | 0938869 | 9/1999 |
| EP | 0613380 | 12/1999 |
| EP | 0993807 | 4/2000 |
| EP | 1074229 | 2/2001 |
| EP | 1077253 | 2/2001 |
| EP | 1120087 | 8/2001 |
| EP | 1129675 | 9/2001 |
| EP | 1132061 | 9/2001 |
| EP | 0732091 | 12/2001 |
| EP | 0814731 | 8/2002 |
| EP | 1234552 | 8/2002 |
| EP | 1234555 | 8/2002 |
| EP | 0809987 | 10/2002 |
| EP | 0833620 | 10/2002 |
| EP | 2124832 | 12/2009 |
| FR | 2819714 | 7/2002 |
| GB | 1451283 | 9/1976 |
| GB | 2291355 | 1/1996 |
| GB | 2348373 | 10/2000 |
| JP | 8-173465 | 7/1996 |
| JP | 9-206322 | 8/1997 |
| JP | 2002-102236 | 4/2002 |
| JP | 2008-537689 | 9/2008 |
| WO | WO 87/02882 | 5/1987 |
| WO | WO 90/009769 | 9/1990 |
| WO | WO 93/004710 | 3/1993 |
| WO | WO 93/009819 | 5/1993 |
| WO | WO 93/025157 | 12/1993 |
| WO | WO 95/027450 | 10/1995 |
| WO | WO 95/028688 | 10/1995 |
| WO | WO 95/030390 | 11/1995 |
| WO | WO 95/032623 | 12/1995 |
| WO | WO 96/024302 | 8/1996 |
| WO | WO 97/025942 | 7/1997 |
| WO | WO 97/026847 | 7/1997 |
| WO | WO 97/027885 | 8/1997 |
| WO | WO 97/038676 | 10/1997 |
| WO | WO 98/012994 | 4/1998 |
| WO | WO 98/20816 | 5/1998 |
| WO | WO 98/030617 | 7/1998 |
| WO | WO 98/32384 | 7/1998 |
| WO | WO 99/002654 | 1/1999 |
| WO | WO 99/008598 | 2/1999 |
| WO | WO 99/008728 | 2/1999 |
| WO | WO 99/042061 | 8/1999 |
| WO | WO 99/047186 | 9/1999 |
| WO | WO 99/051719 | 10/1999 |
| WO | WO 99/056674 | 11/1999 |
| WO | WO 00/009179 | 2/2000 |
| WO | WO 00/015153 | 3/2000 |
| WO | WO 00/035346 | 6/2000 |
| WO | WO 00/048550 | 8/2000 |
| WO | WO 00/059411 | 10/2000 |
| WO | WO 00/074554 | 12/2000 |
| WO | WO 01/010356 | 2/2001 |
| WO | WO 01/017463 | 3/2001 |
| WO | WO 01/019254 | 3/2001 |
| WO | WO 01/035968 | 5/2001 |
| WO | WO 01/045764 | 6/2001 |
| WO | WO 01/068800 | 9/2001 |
| WO | WO 01/070142 | 9/2001 |
| WO | WO 01/091672 | 12/2001 |
| WO | WO 02/000270 | 1/2002 |
| WO | WO 02/000275 | 1/2002 |
| WO | WO 02/002158 | 1/2002 |
| WO | WO 02/022013 | 3/2002 |
| WO | WO 02/022014 | 3/2002 |
| WO | WO 02/023483 | 3/2002 |
| WO | WO 02/034310 | 5/2002 |
| WO | WO 02/036147 | 5/2002 |
| WO | WO 02/096268 | 12/2002 |
| WO | WO 03/007788 | 1/2003 |
| WO | WO 03/037192 | 5/2003 |
| WO | WO 03/047470 | 6/2003 |
| WO | WO 03/051210 | 6/2003 |
| WO | WO 03/055400 | 7/2003 |
| WO | WO 2003/065907 | 8/2003 |
| WO | WO 04/043305 | 5/2004 |
| WO | WO 04/049981 | 6/2004 |
| WO | WO 05/051239 | 6/2005 |
| WO | WO 05/051240 | 6/2005 |
| WO | WO 06/060795 | 6/2006 |
| WO | WO 06/127283 | 11/2006 |
| WO | WO 07/041375 | 4/2007 |
| WO | WO 2007/061983 | 5/2007 |
| WO | WO 07/092841 | 8/2007 |
| WO | WO 08/112996 | 9/2008 |
| WO | WO 08/157412 | 12/2008 |
| WO | WO 2009/001083 | 12/2008 |
| WO | WO 09/111639 | 9/2009 |
| WO | WO2009158522 | 12/2009 |
| WO | WO 2010/099142 | 9/2010 |
| WO | WO 2010/120346 | 10/2010 |
| WO | WO 2010/121147 | 10/2010 |
| WO | WO 2011/110374 | 9/2011 |
| WO | WO2012121726 | 9/2012 |
| WO | WO 2020124052 | 6/2020 |
| WO | WO 2020242542 | 12/2020 |
| WO | WO 2022015877 | 1/2022 |
| WO | WO 2022094052 | 5/2022 |

OTHER PUBLICATIONS

Andersson, et al., "Macintosh Arthroplasty in Rheumatoid Arthritis," Acta. Orthrop. Scand., 1974, pp. 245-259, 45(2).

Argenson, et al., "Is There a Place for Patellofemoral Arthroplasty?, "Clinical Orthopaedics and Related Research No. 321, 1995, pp. 162-167.

Birnbaum, et al., "Computer-Assisted Orthopedic Surgery with Individual Templates and Comparison to Conventional Operation Method," Spine, Feb. 2001, pp. 365-369, vol. 26, No. 4.

Chelule, et al., "Computer Aided Design of Personalized Jigs in Total Knee Replacement," 3rd Annual Meeting of CAOS Int'l Proc., Jun. 18-21, 2003, pp. 58-59, Spain.

Dare, S., Bobyn, J., Drouin, G., Dussault, R., Gariepy, R., "Use of Computerized Tomography and Numerical Control Machining for the Fabrication of Custom Arthroplasty Prostheses." Second World Congress on Biomaterials, 10th Annual Meeting of the Society for Biomaterials, p. 233, Washington, D.C., Apr. 27-May 1, 1984.

DePuy Synthes, "Flexible Reamers for Intramedullary Nails" Surgical Technique, 22 pages, 2017.

De Winter, et al., "The Richards Type II Patellofemoral Arthroplasty," Acta Orthop Scand, 2001, pp. 487-490, 72(5).

(56) References Cited

OTHER PUBLICATIONS

Delp, et al., "A Graphics-Based Software System to Develop and Analyze Models of Musculoskeletal Structures," Comput. Biol. Med., 1995, pp. 21-34, vol. 25, No. 1.
Farrar, et al., "Computed Tomography Scan Scout Film for Measurement of Femoral Axis in Knee Arthroplasty," J. Arthroplasty, 1999, pp. 1030-1031, vol. 14, No. 8.
Final Official Action for U.S. Appl. No. 13/465,547, dated Feb. 26, 2014.
First Office Action for Japanese Patent Appln. No. 2011-552091, dated Oct. 25, 2013.
Froemel, et al., "Computer Assisted Template Based Navigation for Total Knee Replacement," Documents presented at CAOS on Jun. 17, 2001, 4 pages.
Hafez, et al., "Computer Assisted Total Knee Replacement: Could a Two-Piece Custom Template Replace the Complex Conventional Instrumentations?", 4th Annual Meeting of CAOS Int'l Proc., Jun. 16-19, 2004, pp. 63-64, Chicago.
Hafez, et al., "Computer-Assisted Total Hip Arthroplasty: The Present and the Future," Future Rheumatol., 2006, pp. 121-131, vol. 1.
Kim, et al., "Measurement of Femoral Neck Anteversion in 3D. Part 1: 3D Imaging Method," Med. and Biol. Eng. and Computing, 2000, pp. 603-609, vol. 38, No. 6.
Lam, et al., "X-Ray Diagnosis: A Physician's Approach," 1998, Title page and Table of Contents pages Only, ISBN 9813083247, Springer-Verlag publishers.
Lam et al . . . "VarusNalgus Alignment of the Femoral Component in Total Knee Arthroplasty," The Knee, 2003, pp. 237-241, vol. 10.
Lu, et al., "In Vitro Degradation of Porous poly(L-lactic acid) Foams," Biomaterials, Aug. 2000, pp. 1595-1605, 21(15).
Mahaisavariya, et al., "Morphological Study of the Proximal Femur: a New Method of Geometrical Assessment Using 3-Dimensional Reverse Engineering", Medical Engineering & Physics 24 (2002) pp. 617-622.
Marler, et al., "Soft-Tissue Augmentation with Injectable Alginate and Synegeneic Fibroblasts," Plastic & Reconstructive Surgery, May 2000 pp. 2049-2058, 105(6).
PCT/US2010/025143, International Preliminary Report on Patentability and Written Opinion, Sep. 9, 2011.
Portheine, et al., "Potentials of CT-based Planning and Template-based Procedure in Hip and Knee Surgery," Orth. Prac., 2000, pp. 786-791, vol. 36, English Translation with Certification.
Radermacher, "Computer Assisted Matching of Planning and Execution in Orthopedic Surgery," Slide Presentation, Nov. 29, 1993, 22 pages.
Radermacher, "Template Based Navigation—An Efficient Technique for Hip and Knee Surgery," CAOS First Asian Meet, Mar. 27-28, 2004, pp. 45-50, India.
Radermacher, et al., "Computer-Assisted Planning and Operation in Orthopedics," Orth. Prac. 36th Year, Dec. 2000, pp. 731-737, English Translation with Certification.
Rau, et al., "Small and Neat," Medical Tech. Int'l, 1993-94, pp. 65, 67 and 69.
Schkommadau, et al., "Clinical Experience With the Individual Template Technique," Orth. Prac., 2001, pp. 19-22, vol. 37, No. 1, English Translation with Certification.
Seel, et al., "Three-Dimensional Planning and Virtual Radiographs in Revision Total Hip Arthroplasty for Instability," Clinical Orthopaedics and Related Research, Jan. 2006, pp. 35-38, No. 442.
Slone, et al., "Body CT: A Practical Approach," 1999, Title page and Table of Contents pages Only, ISBN 007058219, McGraw-Hill.
Staudte, et al., "Computer-Assisted Operation Planning and Technique in Orthopedics," North Rhine-Westphalia Acad. for Sciences, Lecture N.444, 2000, 17 pages, ISSN 0944-8799, in German.
Staudte, et al., "Computer-Assisted Operation Planning and Technique in Orthopedics," North Rhine-Westphalia Acad. for Sciences, Lecture N.444, 2000, 34 pages, ISSN 0944-8799, English Translation with Certification.
Stauffer, et al., "The Macintosh Prosthesis. Prospective Clinical and Gait Evaluation," Arch. Surg., 1975, pp. 717-720, 110(6).
Stout, et al., "X-Ray Structure Determination: A Practical Guide," 1989, Title page and Table of Contents pages Only, ISBN 0471607118, John Wiley & Sons.
Stryker Trauma GmbH, "Bixcut Reamer System" Osteosynthesis, 8 sheets, 2009.
Synthes, "SynReam, The Synthes Reaming System" Surgical Technique, 22 pages, 2005.
Tamez-Pena, et al., "MRIIsotropic Resolution Reconstruction from Two Orthogonal Scans," Proceedings of the SPIE—The International Society for Optical Engineering SOIE-OMT, 2001, pp. 87-97, vol. 4322.
Testi, et al., "Border Tracing Algorithm Implementation for the Femoral Geometry Reconstruction," Camp. Meth. and Programs in Biomed., 2001, pp. 175-182, vol. 65.
Vandeberg, et al., "Assessment of Knee Cartilage in Cadavers with Dual-Detector Spiral CT Arthrography and MR Imaging," Radiology, Feb. 2002, pp. 430-435, 222(2).
Wiese, et al., "Biomaterial Properties and Biocompatibility in Cell Culture of a Novel Self-Inflating Hydrogel Tissue Expander," J. Biomedical Materials Research Part A, Nov. 2000, pp. 179-188, 54(2).
Woolson, S., Fellingham, L., Dev, P., and Vassiliadis, A., "Three Dimensional Imaging of Bone from Analysis of Computed Tomography Data." Orthopedics, vol. 8, No. 10, pp. 1269-1273, Oct. 1985.
Yusof, et al., "Preparation and Characterization of Chitin Beads as a Wound Dressing Precursor," J. Biomedical Materials Research Part A, Oct. 2000, pp. 59-68, 54(1).
Examination Report issued in connection with corresponding Indian Patent Application No. 2004/KOLNP/2013, Nov. 27, 2018, 7 pages.
First Office Action issued in connection with corresponding Chinese Patent Application No. 201610973637.8, Nov. 28, 2018, 6 pages.
First Examination Repot issued in connection with corresponding Australian Patent Application No. 2018204063, Jul. 10, 2019, 2 pages.
Second Examination Report issued in connection with corresponding Australian Patent Application No. 2019261830, May 4, 2021, 9 pages.
First Examination Repot issued in connection with corresponding Australian Patent Application No. 201926183, Dec. 21, 2020, 4 pages.
International Search Report and Written Opinion issued in connection with International Patent Application No. PCT/US2022/070130, May 13, 2022, 17 pages.

* cited by examiner

IMPLANT PEG WITH MULTIPLE COMPONENTS

CROSS-REFERENCE TO RELATED APPLICATION

This application claims benefit to U.S. Provisional Application No. 63/153,040, filed Feb. 24, 2021, entitled "Implant Peg with Multiple Components," the disclosure of which is incorporated herein by reference in its entirety.

FIELD

This disclosure relates generally to medical devices, and specifically to bone implants.

BACKGROUND

An ankle joint may become severely damaged and may be treated by total ankle replacement. One type of total ankle replacement comprises two components; one part is implanted in a resected tibia and the other part is implanted in a resected talus. The talar implant can include a stem and/or one or more pegs, screws or combinations of pegs, screws and stem that extend into openings drilled into the resected surface of the bone.

SUMMARY

According to one aspect, a novel tibial tray component of an ankle replacement prosthesis is disclosed. The tibial tray of the present disclosure is a modular system that allows the surgeon to have different fixation options when implanting the tibial component. The surgeon will be able to select among pegs, screws, and/or variations of stems. The tibial tray can also include other features that can also increase the tibial tray's stability in the bone after implantation.

In some embodiments, the tibial tray comprises a tibial-facing surface, a lower surface opposite the tibial-facing surface, a medial surface, a lateral surface, an anterior end, and a posterior end, wherein the tibial-facing surface is configured for receiving one or more modular fixation elements.

According to another aspect, disclosed is an ankle replacement prosthesis comprising a tibial tray that comprises a tibial-facing surface, a lower surface opposite the tibial-facing surface, a medial surface, a lateral surface, an anterior end, and a posterior end, wherein the tibial-facing surface is configured for receiving one or more modular fixation elements. The ankle replacement prosthesis further comprises a talar plate for engaging a resected surface on a talus, and a tibial implant that fits between the tibial tray and the talar plate. The tibial implant comprises an anterior end and a posterior end and a tibial-facing surface and a talar-facing surface.

A novel orthopedic peg for fastening an orthopedic plate to a bone is also disclosed. The orthopedic peg comprises a head comprising a locking threaded surface, and a body portion extending from the head and having a length, wherein the body portion is continuously tapered over the length starting near the head.

A system is disclosed which comprises an orthopedic plate, and at least one of the orthopedic pegs for fastening the orthopedic plate to a bone.

BRIEF DESCRIPTION OF THE DRAWINGS

The description of the exemplary embodiments disclosed herein are intended to be read in connection with the accompanying drawings, which are to be considered part of the entire written description. All drawing figures are schematic illustrations and are not intended to show actual dimensions or proportions.

DETAILED DESCRIPTION

Figure 1A:
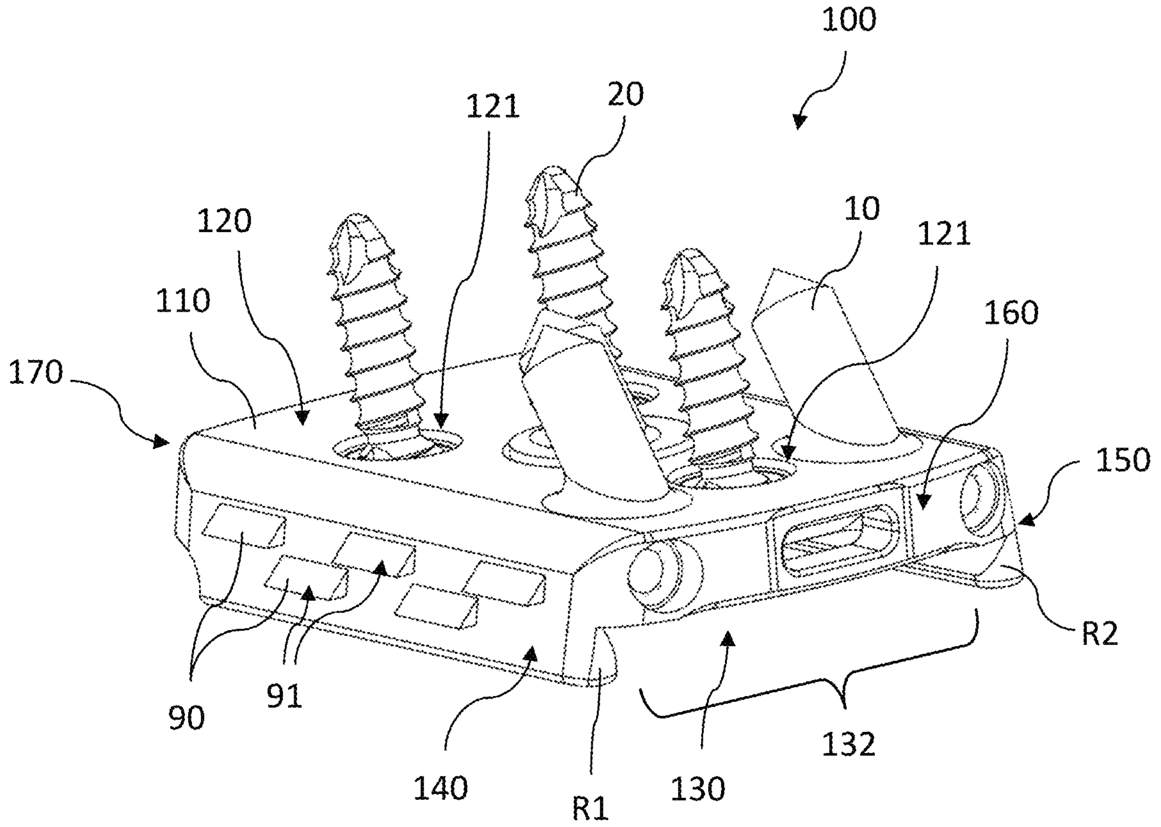
FIGS. 1A-1B are illustrations of a tibial tray implant assembly according to an embodiment.

This description of the exemplary embodiments is intended to be read in connection with the accompanying drawings, which are to be considered part of the entire written description. The drawing figures are not necessarily to scale, and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Referring to FIGS. 1A-5I, various embodiments of a novel tibial tray assembly that utilizes a modular fixation elements that provides the surgeon to have options when implanting the tibial tray in a total ankle replacement procedure. The modular feature of the tibial tray allows the surgeon to select from a variety of pegs, screws, and/or variations of stems as the fixation elements to secure the tibial tray to the patient's tibia. The tibial tray of the present disclosure can also comprise other beneficial features that enhance the stability of the tibial tray in the tibia.

FIG. 1A is an illustration of a tibial tray 100 for an ankle replacement prosthesis according to an embodiment. The tibial tray 100 comprises a substrate 110 that comprises a tibial-facing surface 120, a lower surface 130 opposite the tibial-facing surface 120, a medial surface 140, a lateral surface 150, an anterior end 160, and a posterior end 170, wherein the tibial-facing surface 120 is configured for receiving one or more modular fixation elements.

Figure 1B:
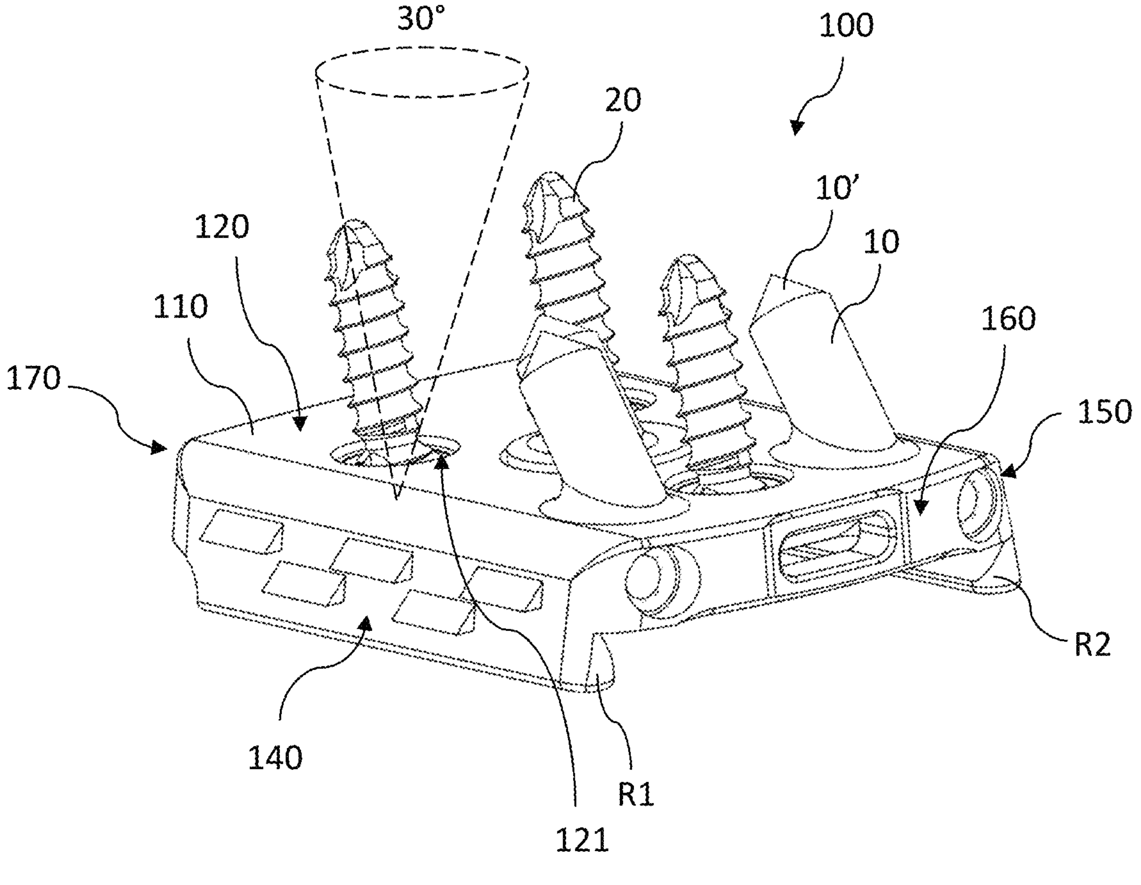

In some embodiments, the tibial-facing surface 120 comprises one or more threaded holes 121 for receiving the one or more modular fixation elements at a desired angle. The modular fixation elements are configured to engage the threaded holes 121 in a removable manner. The threaded holes 121 are configured to receive a modular fixation element at variable angles of up to 15° off the center axis of the threaded holes 121. In other words, the threaded holes 121 are configured to receive a modular fixation element, such as a screw, with a 30° conical range of angulation. This is illustrated in FIG. 1B. In some embodiments, the desired angle is an acute angle with respect to the tibial-facing surface 120 such that the modular fixation elements are leaning toward the posterior end 170.

In some embodiments, the tibial tray 100 can also comprise one or more non-modular (i.e. fixed) fixation elements. The non-modular fixation elements can be pegs of different lengths, different diameters, and can extend from the tibial tray 100 at any desired angles. For example, the tibial tray 100 shown in FIG. 1 is configured with three fixed pegs 10 and three modular fixation elements that are screws 20. Each of the fixed peg 10 has a fixed angulation and orientation.

The modular fixation elements can be screws 20 as in the example tibial tray 100 or they can be pegs or stems. Regardless of the type, the modular fixation elements comprise a threaded head that threadedly engage the one or more internally threaded holes 121 provided in the tibial tray 100. The threaded head of the screw 20 can be configured to be a locking type or a non-locking type. Similar to the locking bone screws used in certain bone plates, the threaded head of the modular fixation elements are configured to be able to lock with the tibial tray 100 at any desired angle and orientation within the above-mentioned 30° conical range of angulation. The detailed structures of such threaded head and the corresponding internally threaded holes 121 are well known to those skilled in the art.

In some embodiments of the tibial tray 100, the tibial-facing surface 120 is configured for receiving two or more modular fixation elements that comprise at least one fixation peg 10 and at least one fixation screw 20. In the illustrated example of the tibial tray 100 in FIG. 1, the tibial-facing surface 120 is configured for receiving three fixation pegs 10 and three fixation screws 20.

Figure 2A:
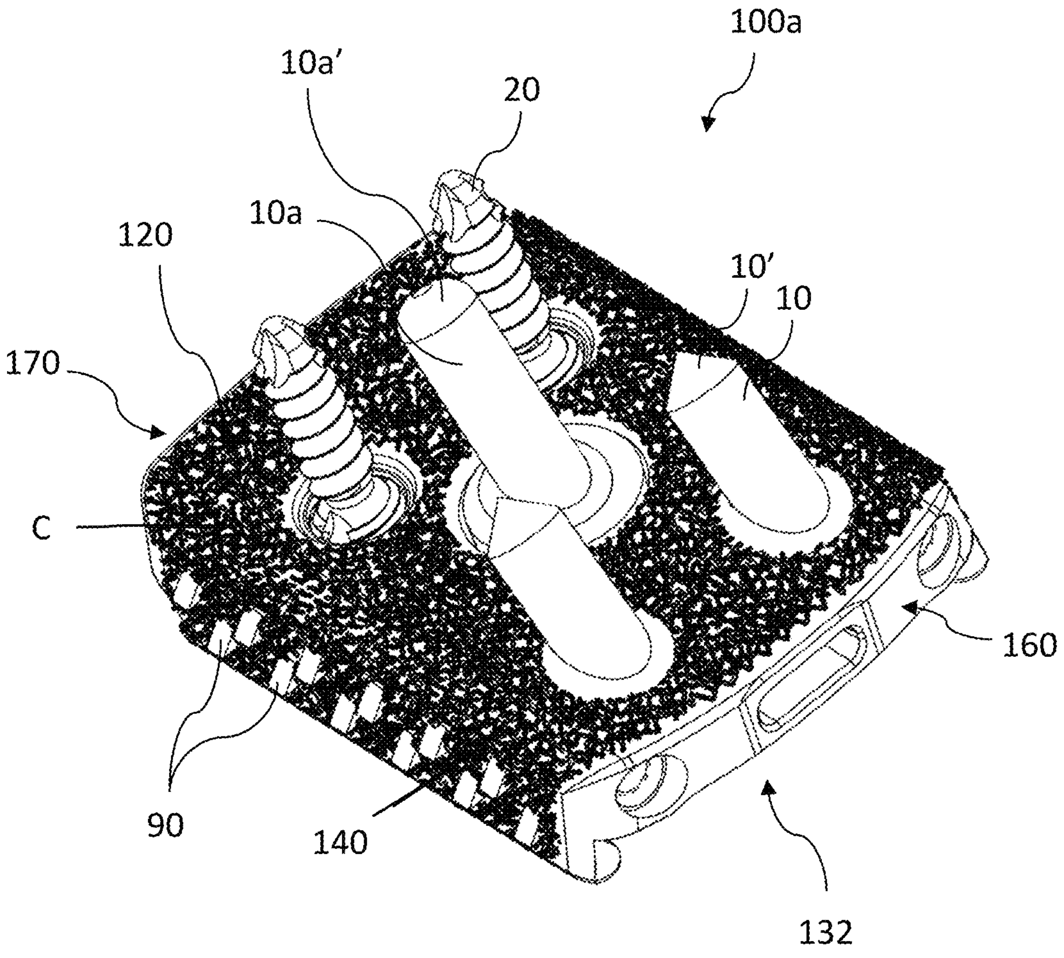
FIG. 2A is an illustration of a tibial tray implant according to another embodiment.
Figure 2B:
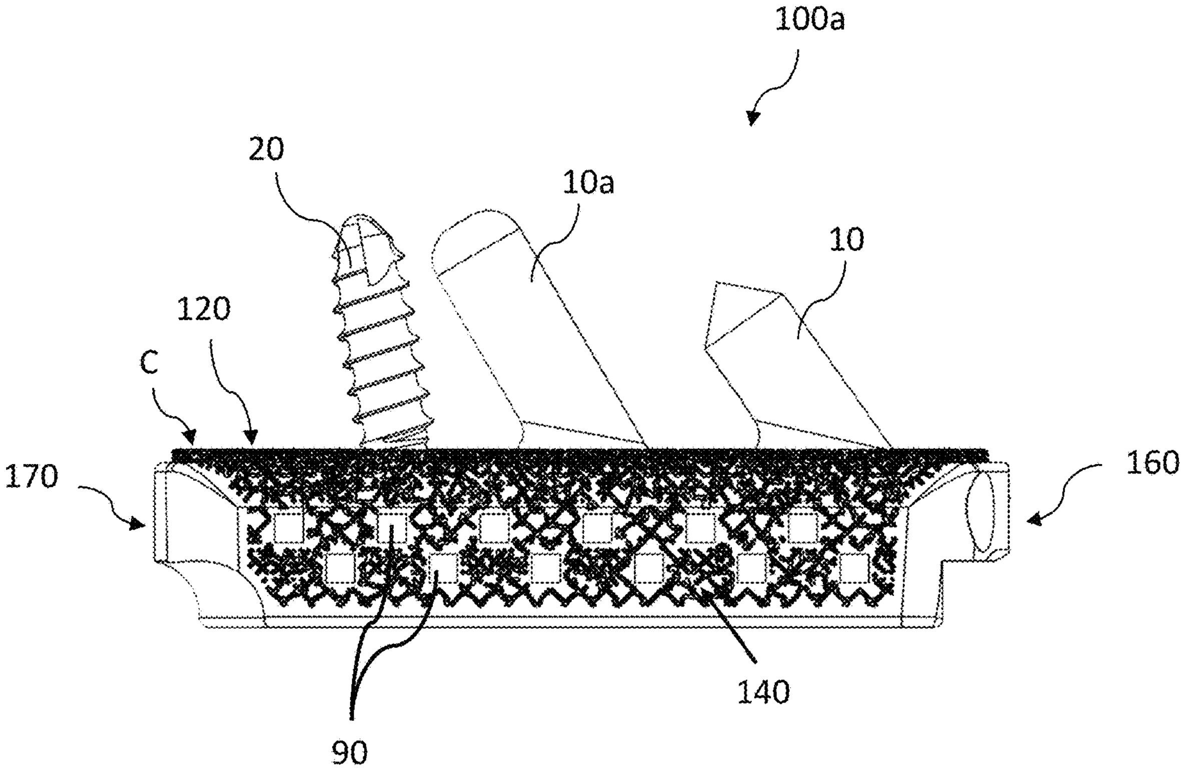
FIG. 2B is a view of the tibial tray implant of FIG. 2A seen from the medial side.
Figure 2C:
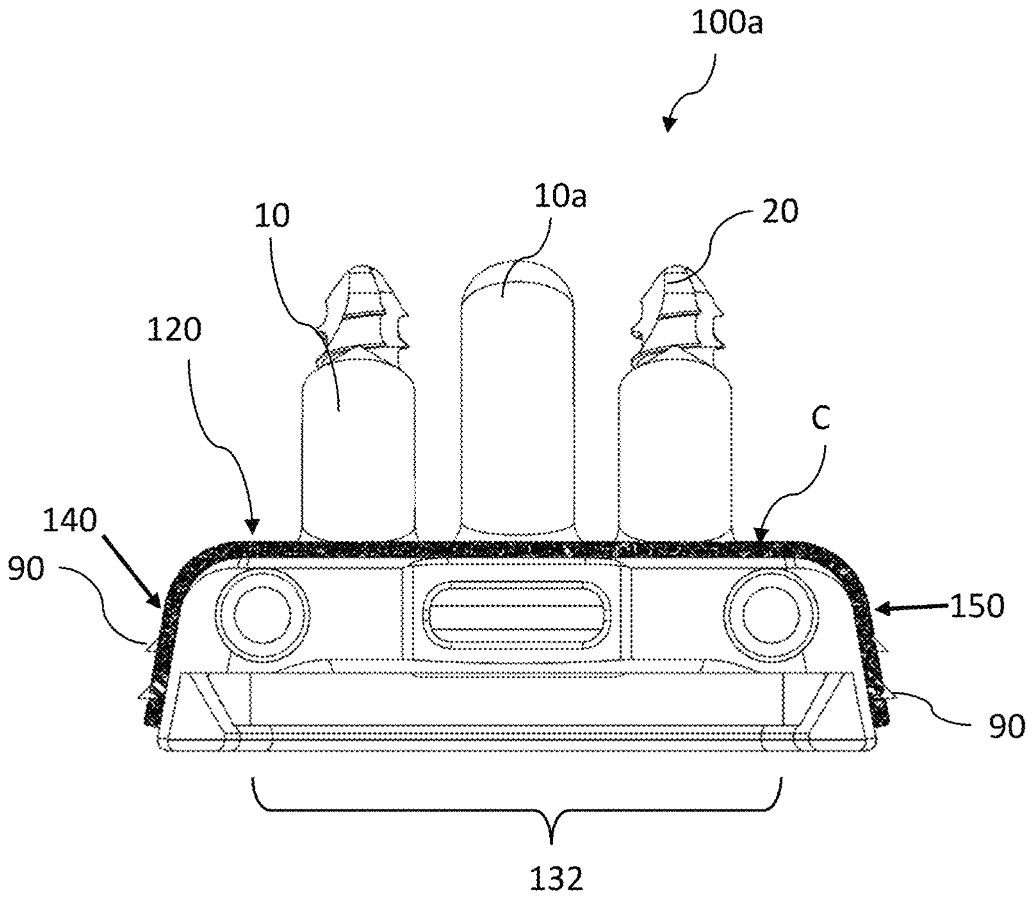
FIG. 2C is a view of the tibial tray implant of FIG. 2A seen from the anterior side.
Figure 2D:
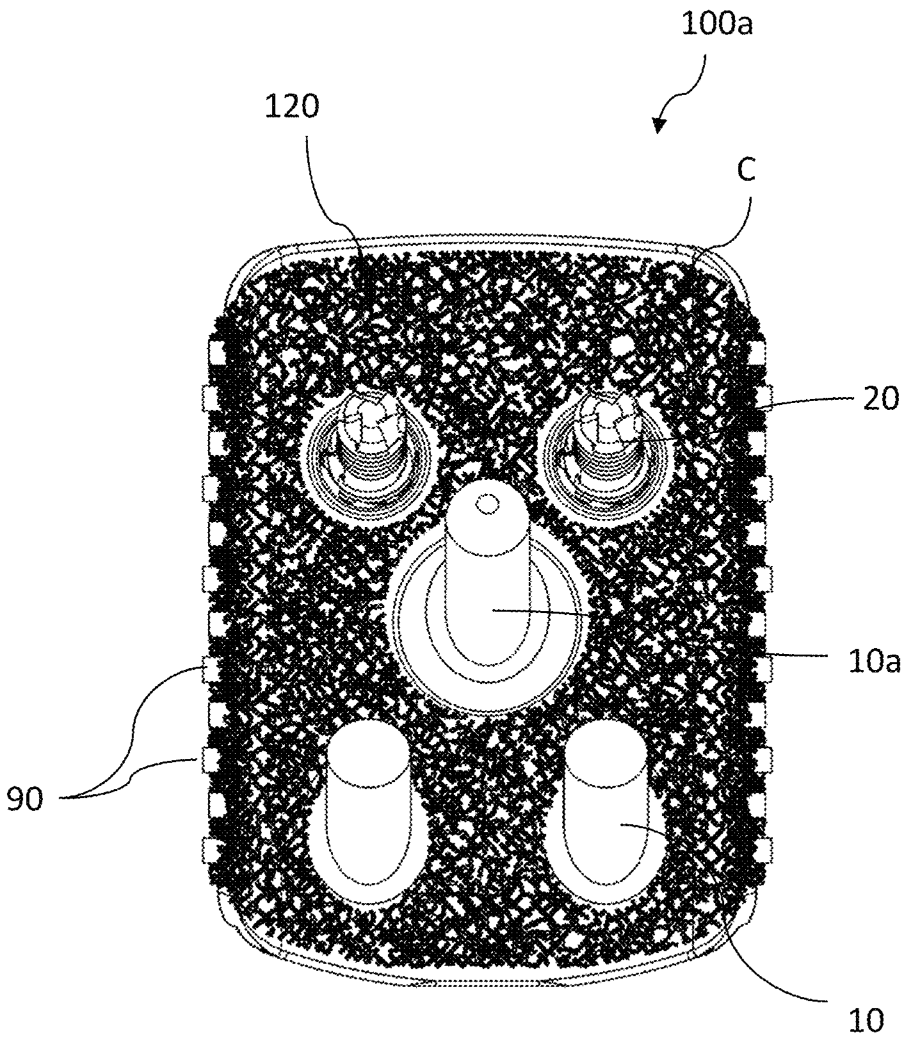
FIG. 2D is a view of the tibial tray implant of FIG. 2A seen from above the tibial-facing surface 120.

In the illustrated example of the tibial tray 100*a* in FIG. 2A, the tibial-facing surface 120 is configured for receiving three fixation pegs 10, 10*a*, and two fixation screws 20. The tips of the fixation pegs can be configured with different shapes as needed. In the example in FIG. 2A, the two outer fixation pegs 10 have conical tips 10' while the central fixation peg 10*a* has a rounded tip 10*a'*.

Figure 2E:
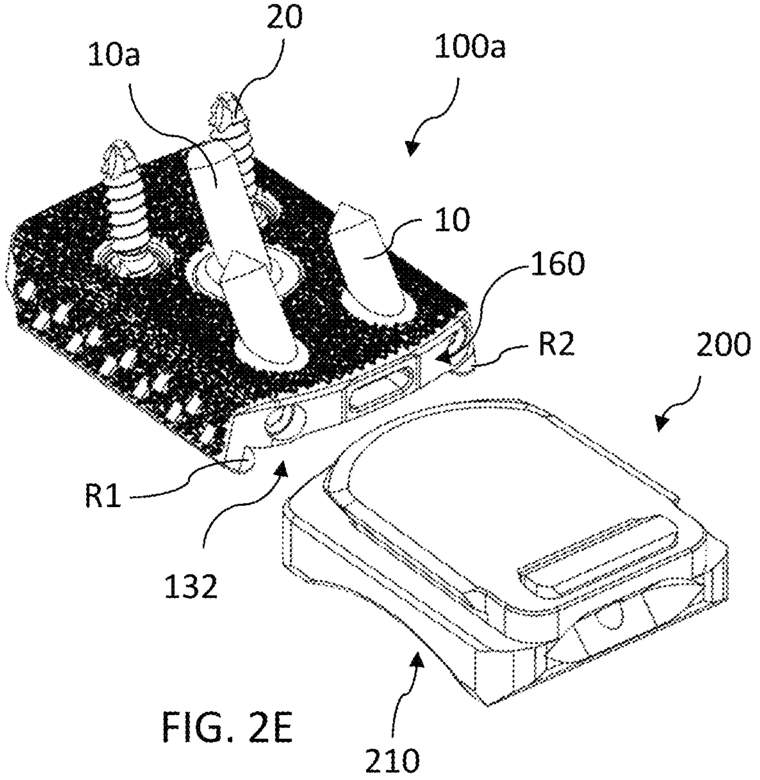
FIGS. 2E and 2F are illustrations showing an example of the tibial tray of FIG. 2A with a tibial insert.
Figure 2F:
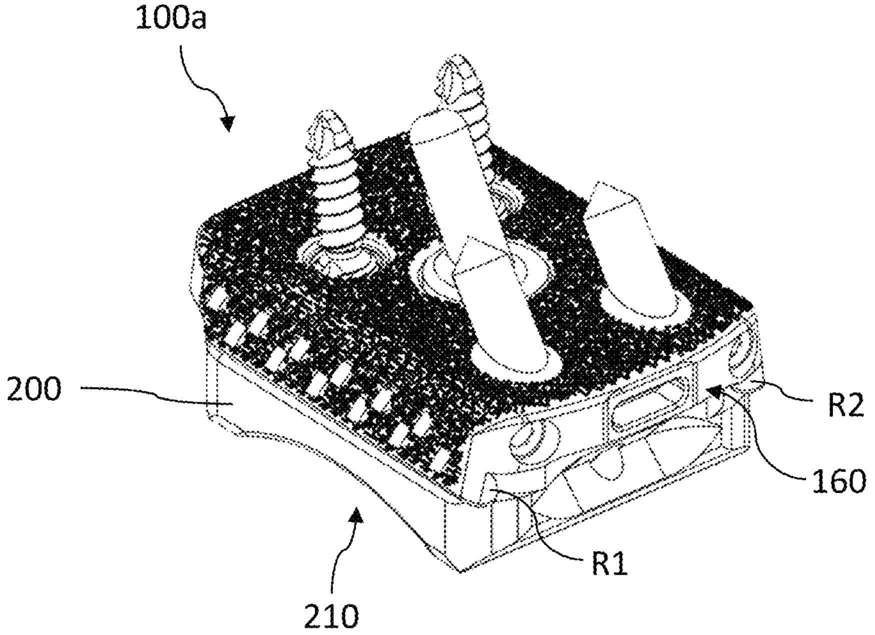

In some embodiments of the tibial tray 100, 100*a*, the lower surface 130 further comprises a cutout region 132 therein configured for slidably receiving a removable tibial insert 200. In FIGS. 2E and 2F, an example of the tibial tray 100*a* is shown with a tibial insert 200. The tibial insert 200 comprises a bearing surface (or an articulating surface) 210 for engaging an anatomical talus bone or a talus implant. The cutout region 132 is configured to receive the tibial insert 200 via an entrance region provided at the anterior end 160 of the tibial tray 100, 100*a*. The cutout region 132 comprises two opposing side rails R1, R2 for slidably receiving the tibial insert 200.

Referring to FIGS. 1A-2A, in some embodiments, the tibial tray 100, 100*a* can comprise a plurality of protruding ridges or barbs 90 provided on the medial surface 140 and lateral surface 150 for augmenting the medial and lateral tibial interface to enhance the stability of the tibial tray 100, 100*a* in the tibial bone. The protruding ridges 90 are configured to engage the resected tibial surfaces corresponding to the medial surface 140 and the lateral surface 150 on the tibial tray 100, 100*a* and enhance the stability of the implant/tibial interface formed between the medial 140 and lateral surfaces 150 and a tibia.

In some embodiments, each of the plurality of protruding ridges 90 comprises a surface 91 that flares outward from an end closer to the tibial-facing surface 120 towards the lower surface 130. In other words, the protruding ridges 90 have a wedge shape with the wider part of the wedge facing the lower surface 130 of the tibial tray 100, 100*a*. Thus, the protruding ridges 90 help prevent the tibial tray 100, 100*a* from backing out of the tibia after implantation.

Referring to FIGS. 2A-2D, a tibial tray 100*a* is provided according to another embodiment of the present disclosure. The tibial tray 100*a* further comprises additional fixation features such as a porous metallic material coating C on the tibial-facing surface 120, the medial surface 140, and the lateral surface 150 to promote bone ingrowth to further enhance the tibial tray's fixation with the surrounding tibial bone. An example of such porous metallic material is Wright Medical Technology's ADAPTIS™. In FIG.

In the example tibial tray 100*a* in FIG. 2A, the tibial tray is configured with three fixed fixation elements an two internally threaded holes 121 for receiving up to two modular fixation elements. In the illustrated example, the two modular fixation elements are screws 20. The two fixed fixation elements are two fixed pegs 10 and one tibial stem 10*a*.

Figure 3A:
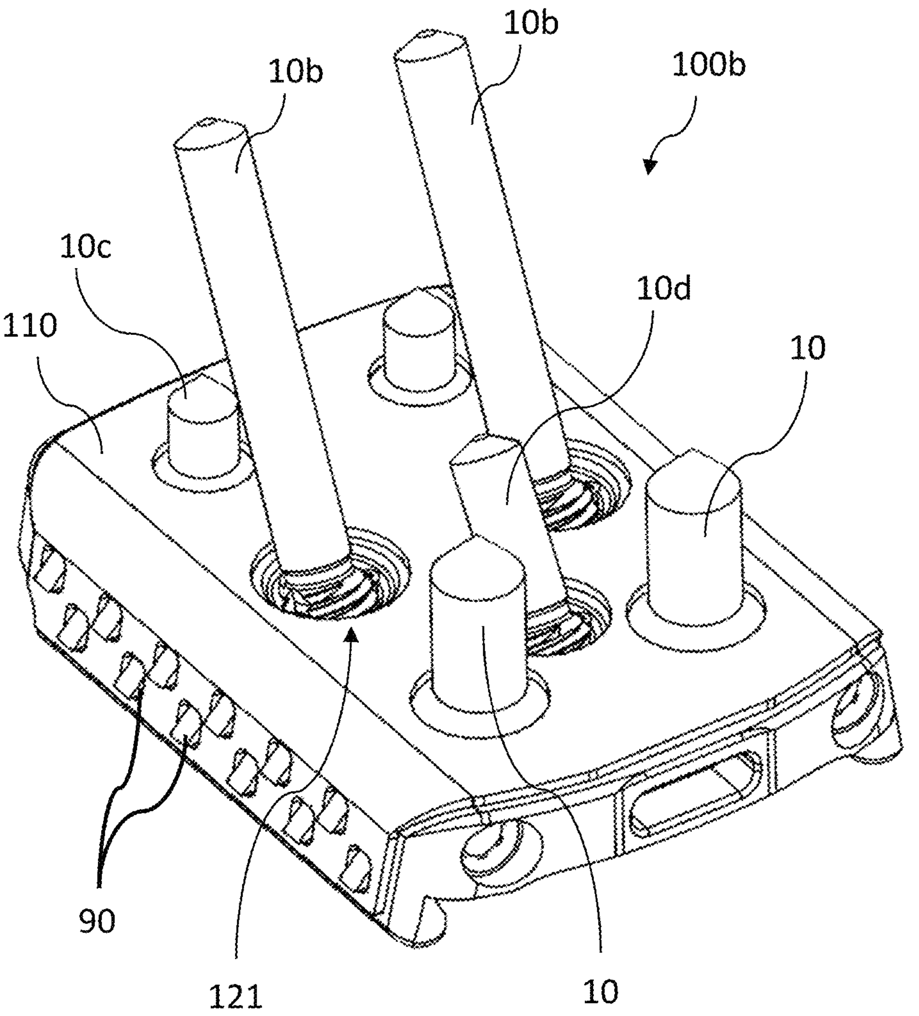
FIG. 3A is an isometric view of a tibial tray implant according to another embodiment.
Figure 3B:
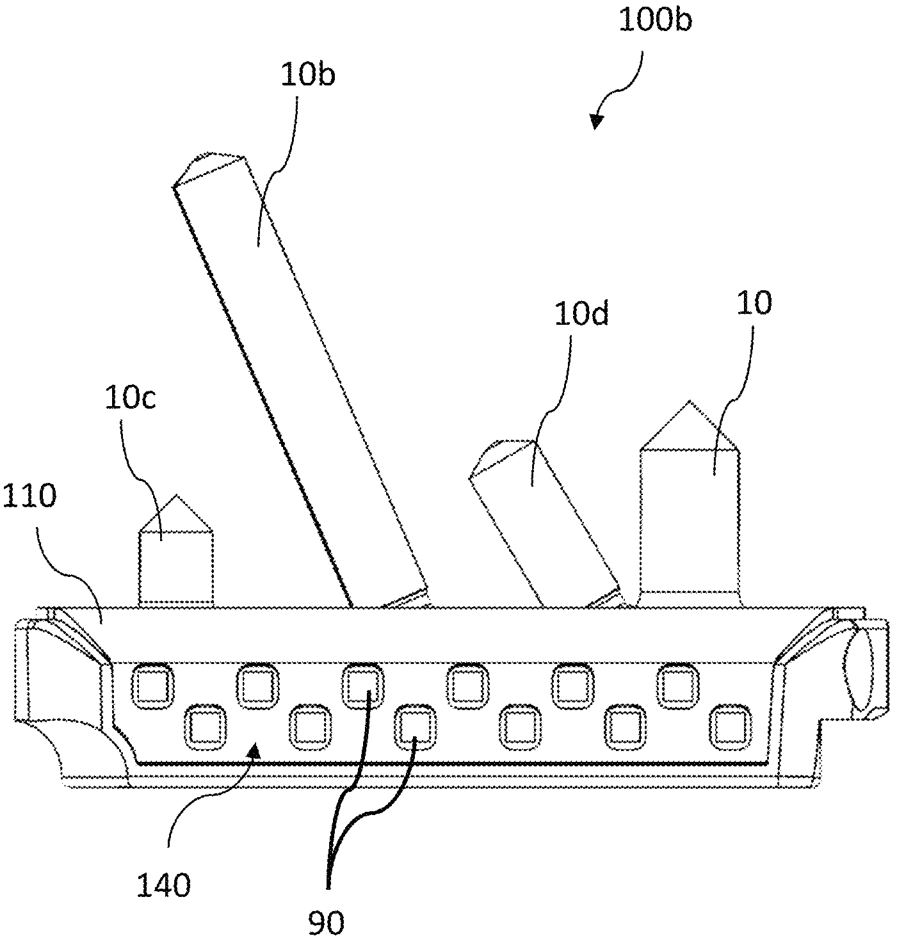
FIG. 3B is a view of the tibial tray implant of FIG. 3A seen from the medial side.
Figure 3C:
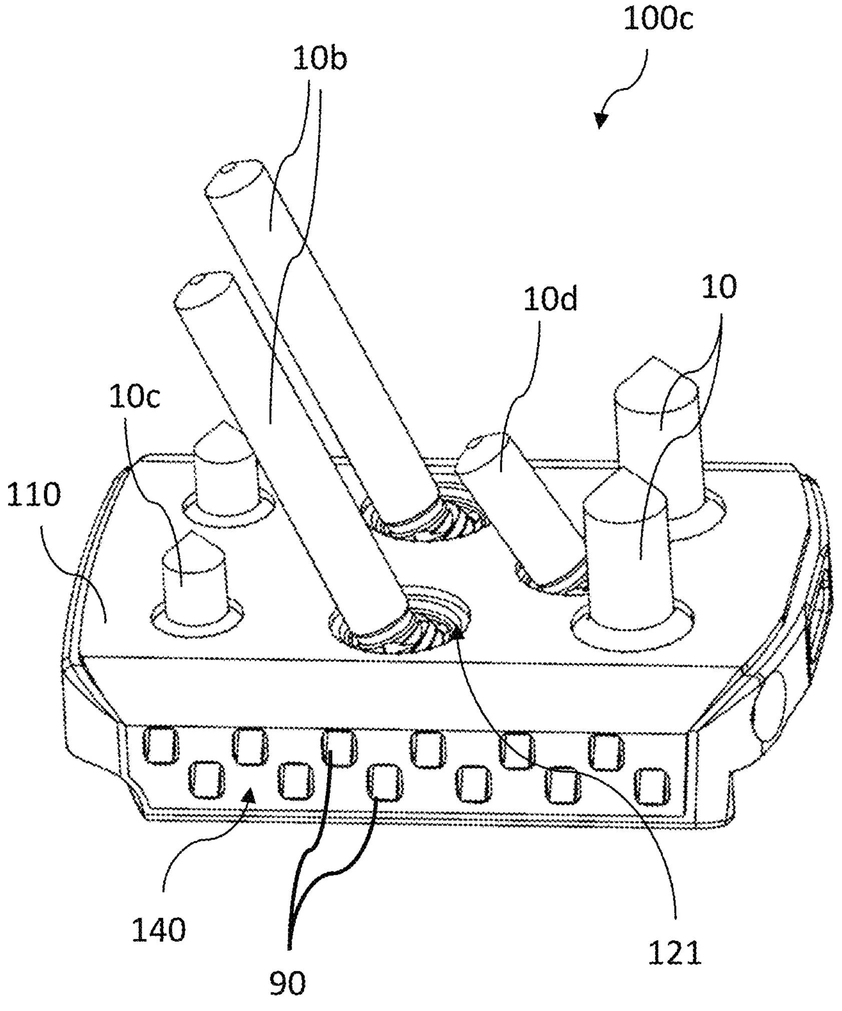
FIG. 3C is an elevated isometric view of the tibial tray implant of FIG. 3A seen from the medial side.

FIGS. 3A-3C are illustrations showing a tibial tray 100*b* according to another embodiment of the present disclosure. The tibial tray 100*b* is configured with four fixed fixation elements that are pegs 10, 10*c*, and is configured with three internally threaded holes 121 for receiving up to three modular fixation elements. Depending on the needs of the particular patient, the modular fixation elements can be screws, pegs, or a stem. FIGS. 3A-3C show an example where the three modular fixation elements are modular pegs 10*b* and 10*d*. In some embodiments, the modular fixation elements can be provided in different lengths as appropriate. In the tibial tray 100*b* example, the two modular pegs 10*b* are longer than the modular peg 10*d*.

Figure 4A:
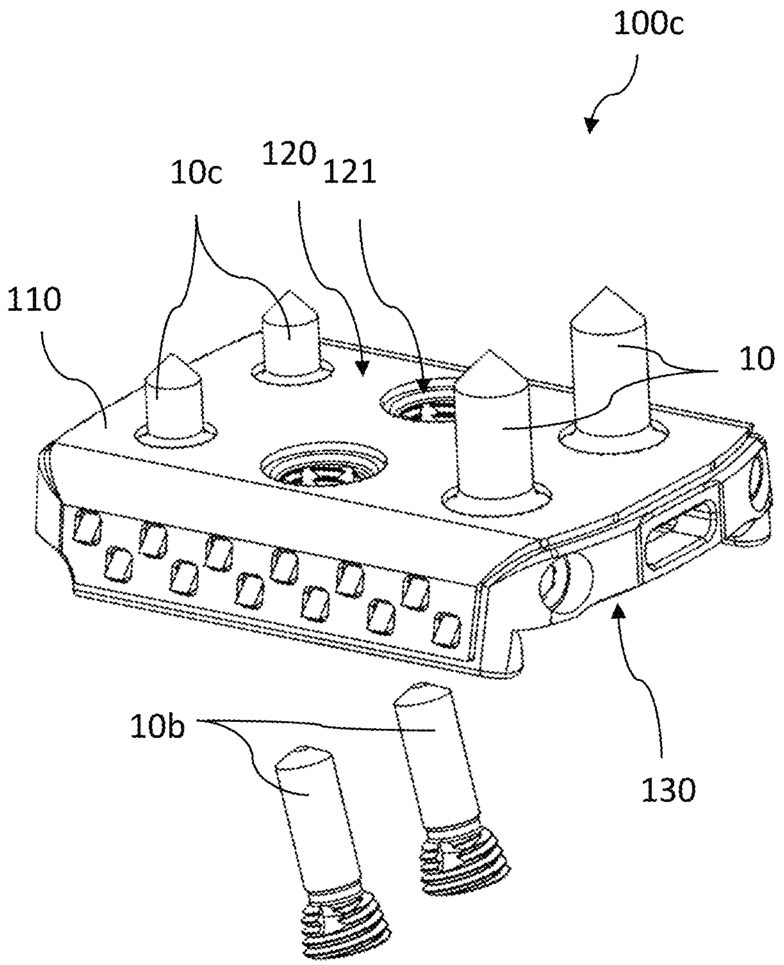
FIGS. 4A-4E are illustrations of a tibial tray implant according to another embodiment.
Figure 4B:
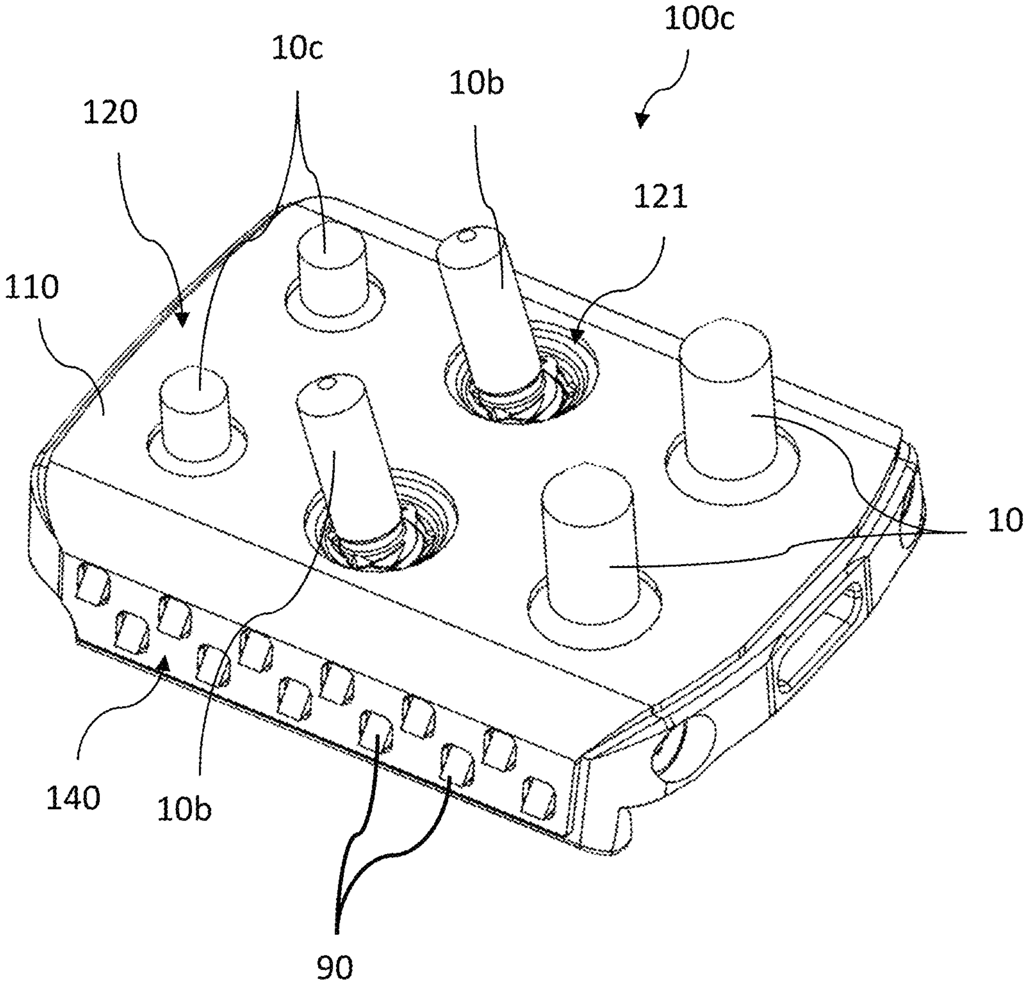
Figure 4C:
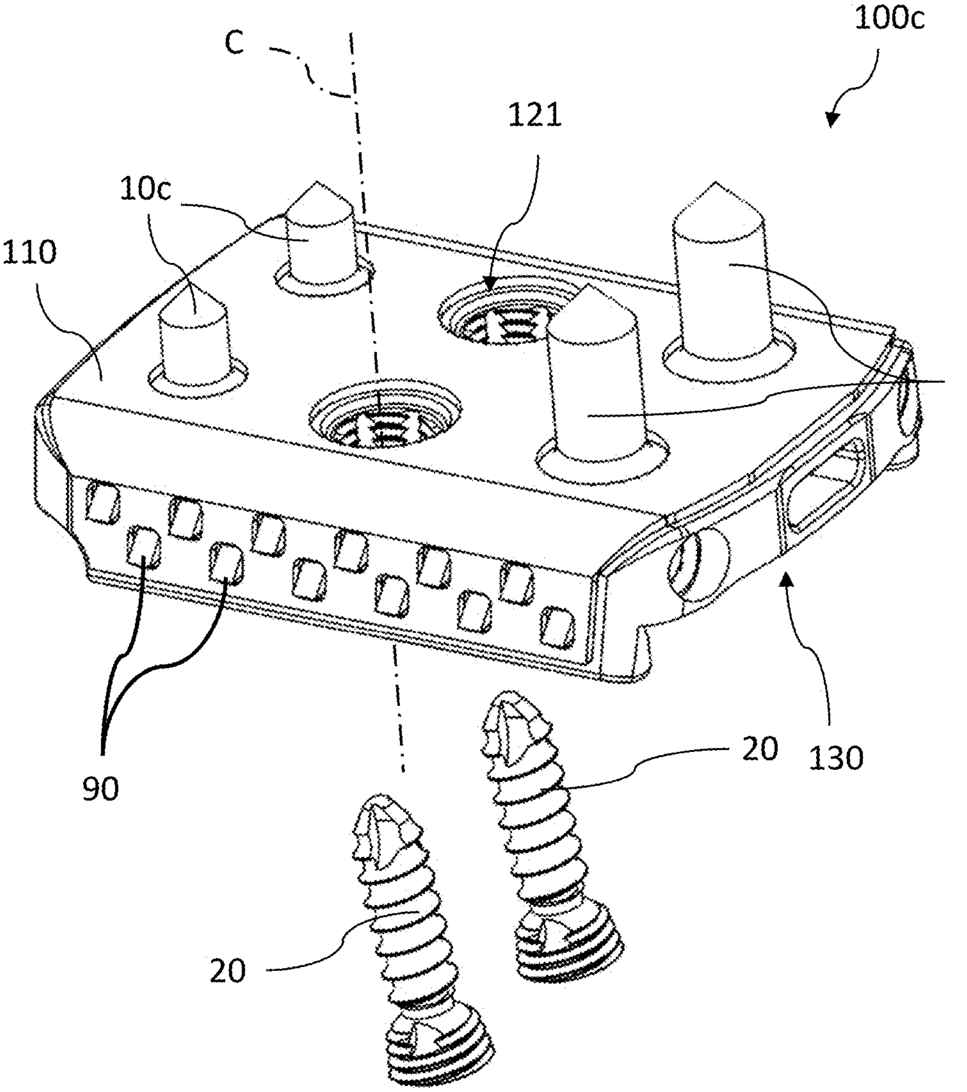
Figure 4D:
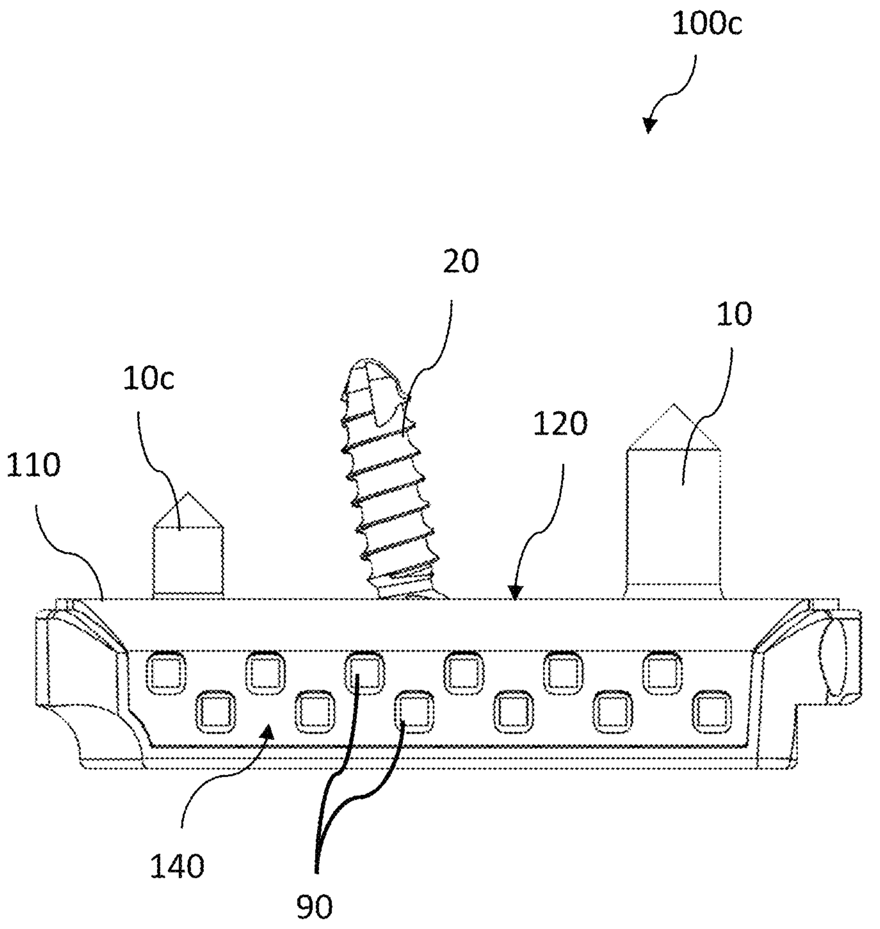
Figure 4E:
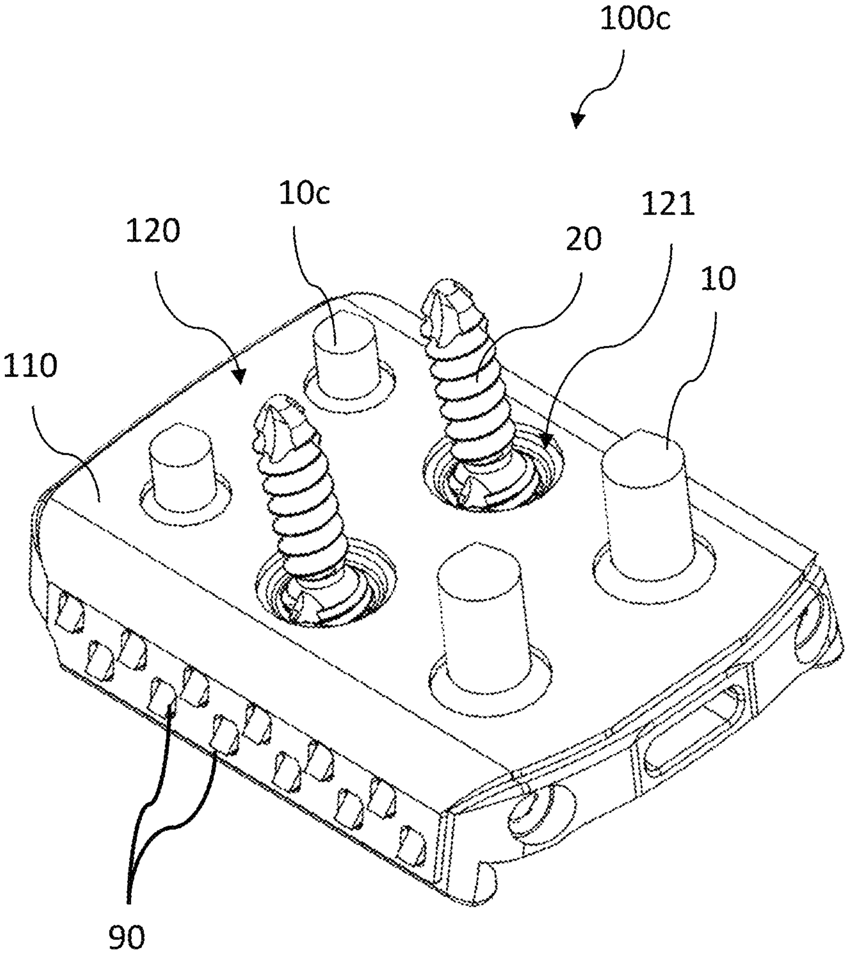

FIGS. 4A-4E are illustrations showing a tibial tray 100*c* according to another embodiment of the present disclosure. The tibial tray 100*c* is configured with four fixed fixation elements that are pegs 10, 10*c*, and is configured with two internally threaded holes 121 for receiving up to two modular fixation elements. Depending on the needs of the particular patient, the modular fixation elements can be screws, pegs, or a stem. FIG. 4B shows an example where the two modular fixation elements are pegs 10*b*. FIGS. 4C-4D show an example where the two modular fixation elements are screws 20. As shown in FIGS. 4A and 4C, the internally threaded holes 121 in the tibial tray 100*c* can be configured to receive the modular fixation elements from the lower surface 130.

FIGS. 5A-5I are illustrations showing a tibial tray 100*d* according to another embodiment of the present disclosure. The tibial tray 100*d* is configured with two internally threaded holes 121 for receiving up to two modular fixation elements. Depending on the needs of the particular patient, the modular fixation elements can be screws, pegs, or a stem.

Figure 5A:
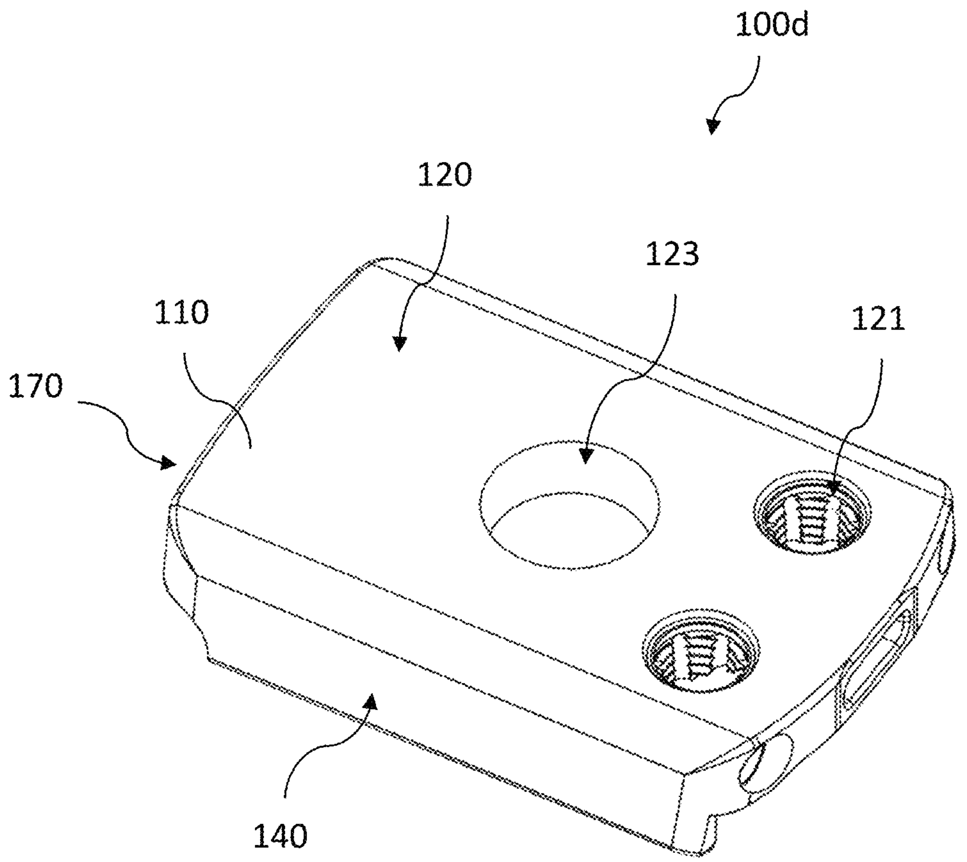
FIG. 5A-5I are illustrations of a tibial tray implant according to another embodiment.
Figure 5B:
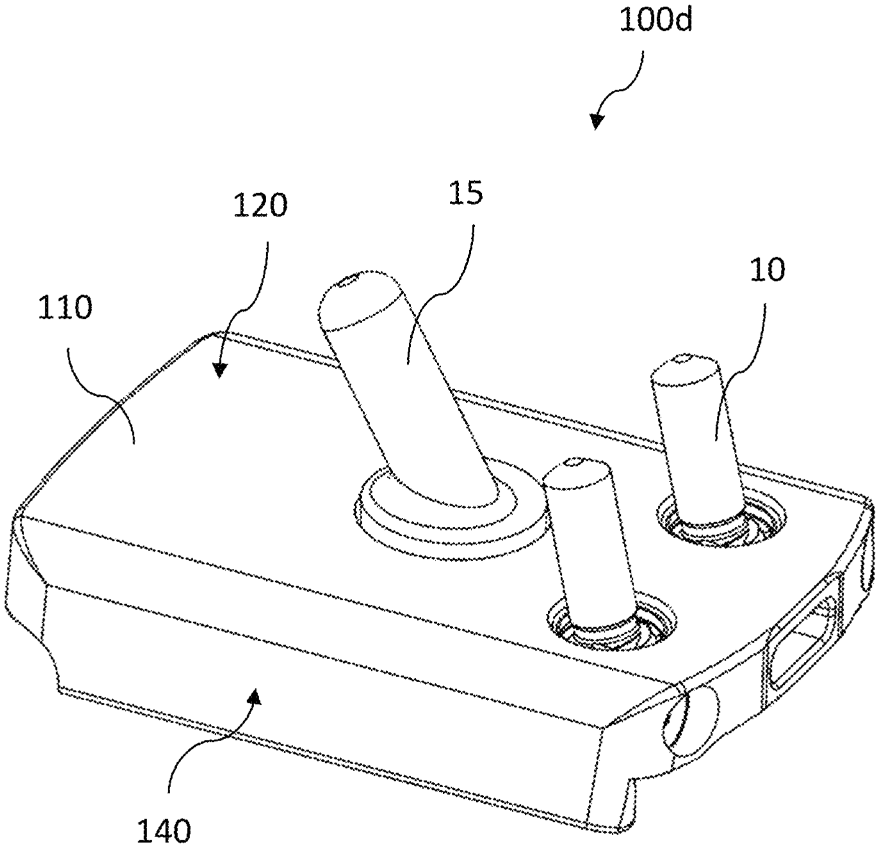
Figure 5C:
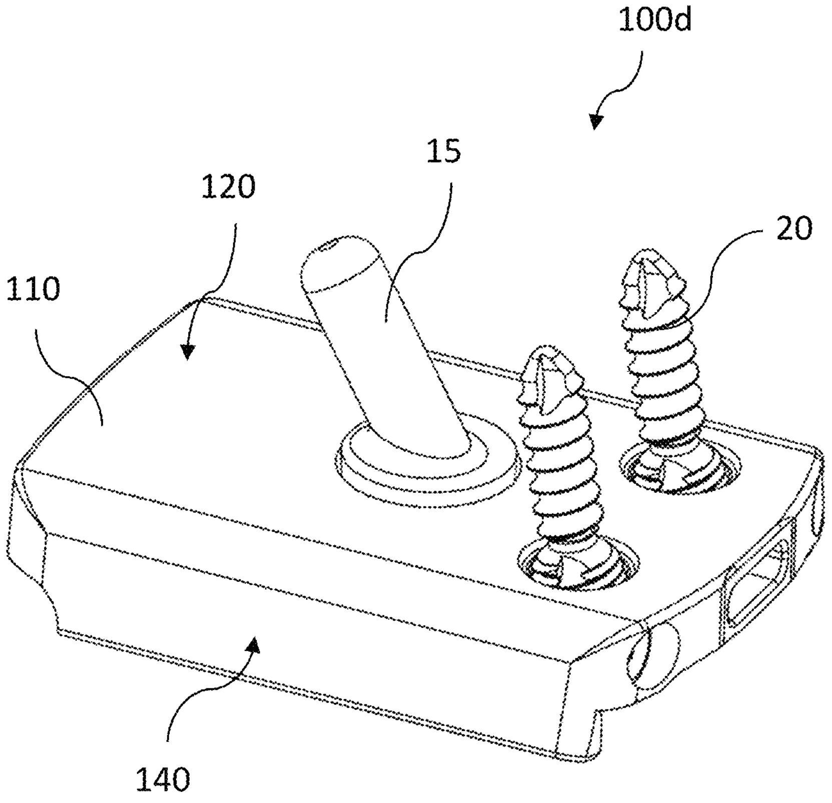

As shown in FIG. 5A, the tibial tray 100*d* can be further configured with a central non-threaded hole 123 for receiving a modular fixation element that is a central peg or a tibial stem. FIG. 5B shows an example where a modular central peg 15 that is inserted into the central non-threaded hole 125 and two modular pegs 10 that are inserted into the internally threaded holes 121. The central non-threaded hole 123 is a tapered hole (i.e., Morse taper) that solidly locks central peg 15 to tibial tray without having to turn the central peg as would be required for threaded locking. The tapered hole can also be used to connect a locking plug or tibial stem. In the illustrated example in FIG. 5C, two screws 20 are inserted into the internally threaded holes 121.

Figure 5D:
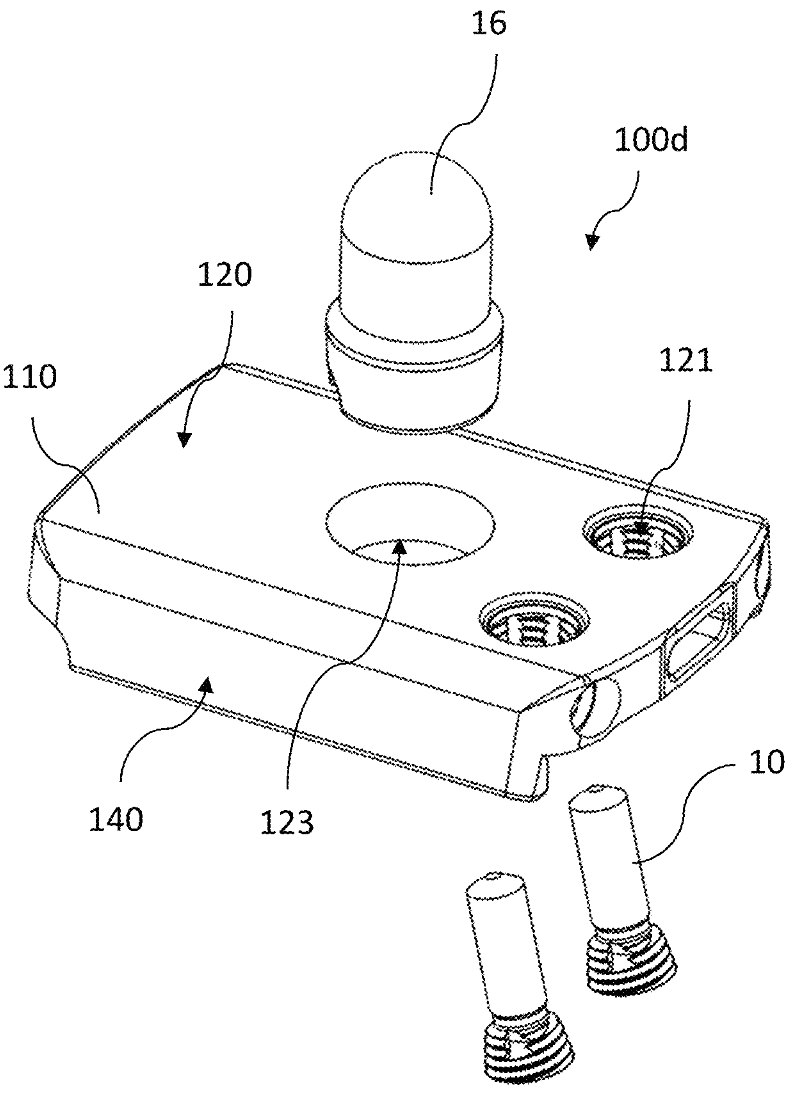
Figure 5E:
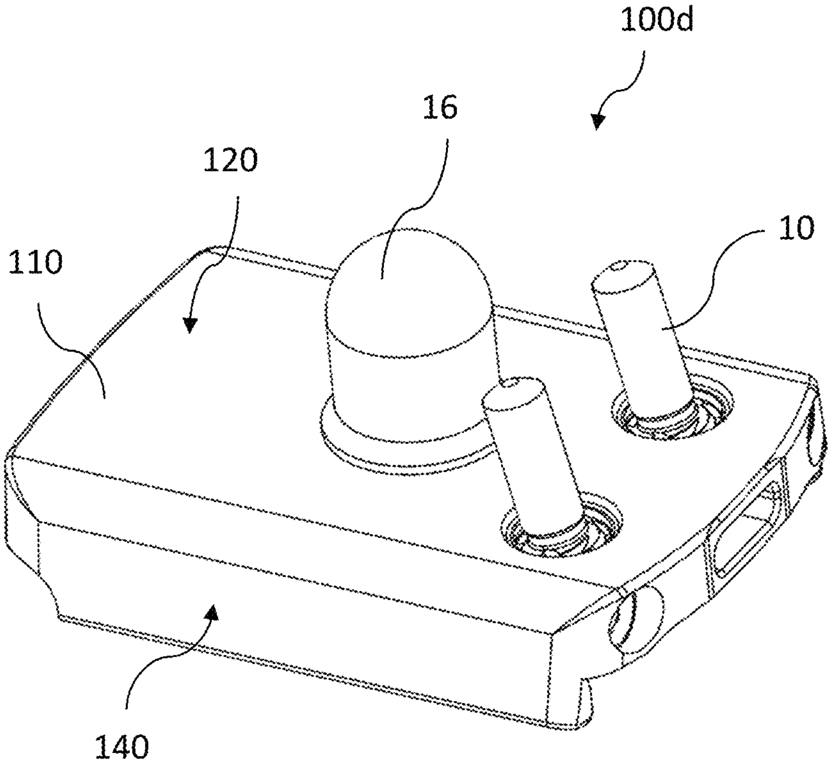

FIG. 5D shows an example where the tibial tray 100*d* is being configured with two modular pegs 10 and one modular central short tibial stem 16 that is inserted into the non-threaded hole 123. The components are shown in exploded view. FIG. 5E shows the modular central short tibial stem 16 and the two modular pegs 10 in place.

Figure 5F:
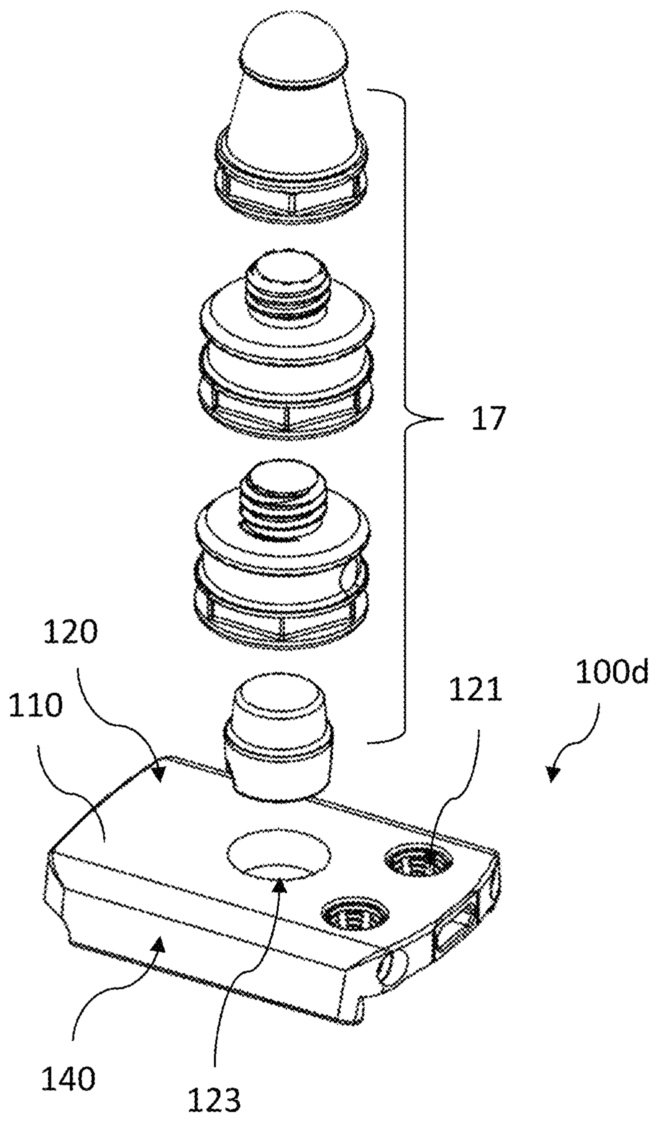
Figure 5G:
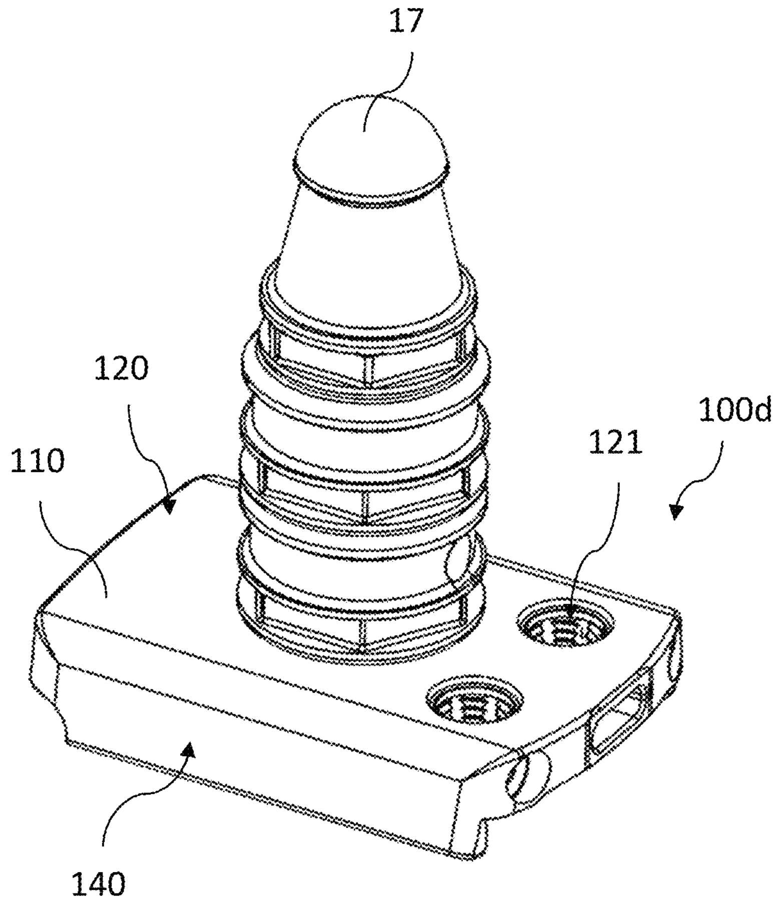
Figure 5H:
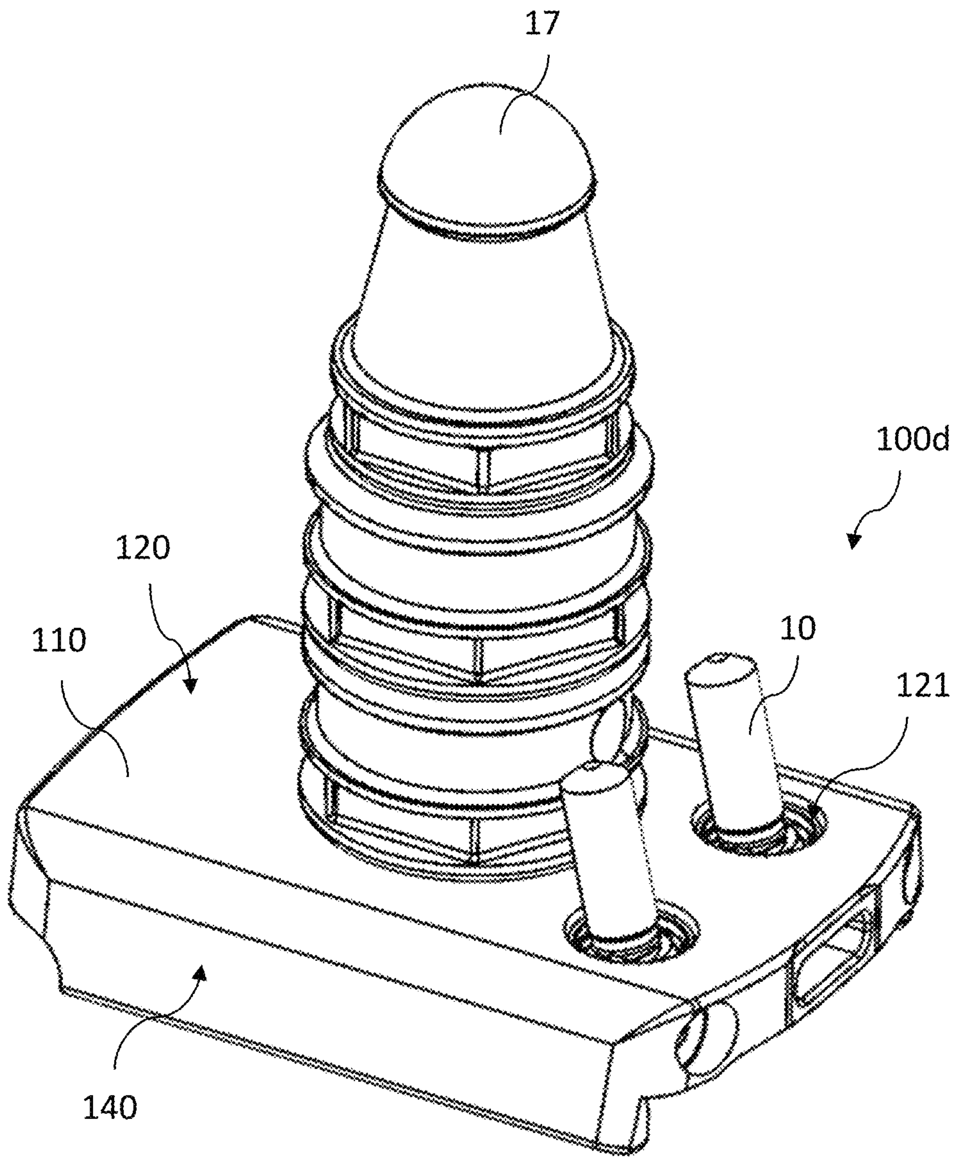
Figure 5I:
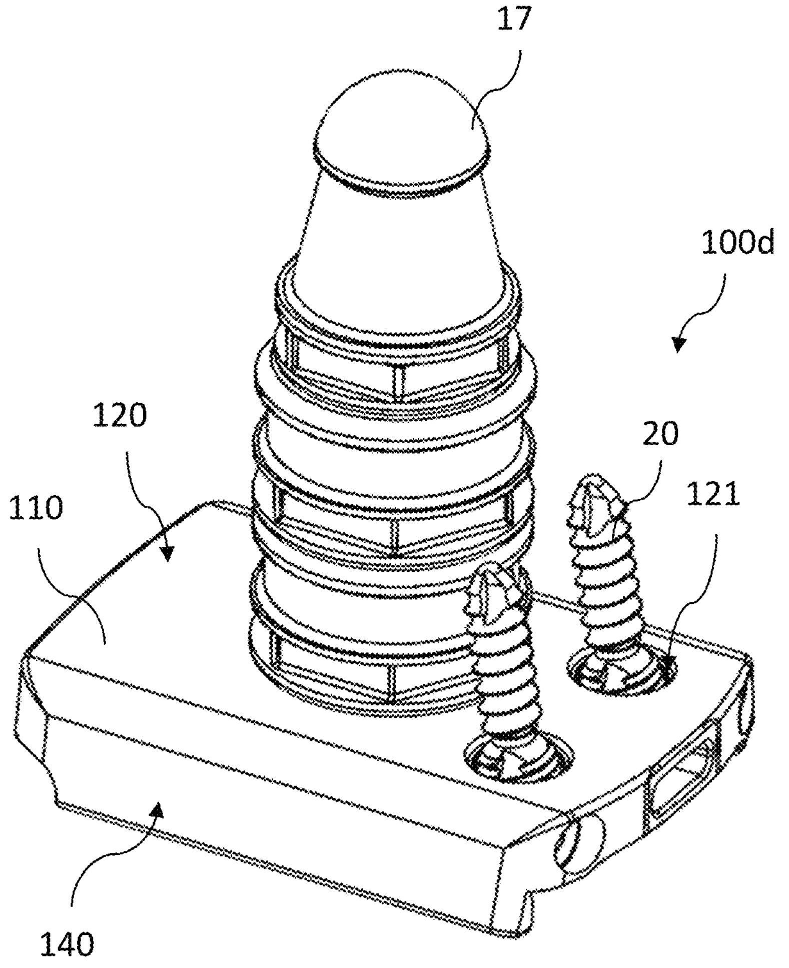

FIG. 5F shows an exploded view of an example where the tibial tray 100*d* is being configured with a modular tibial stem 17 into the non-threaded hole 123. FIG. 5G shows the modular tibial stem 17 in an assembled configuration. FIG. 5H shows the tibial tray 100*d* with two modular pegs 10 locked into the internally threaded holes 121. FIG. 5I shows the tibial tray 100*d* with two modular screws 20 locked into the internally threaded holes 121.

[Tapered Talar Pegs]

Figure 6A:
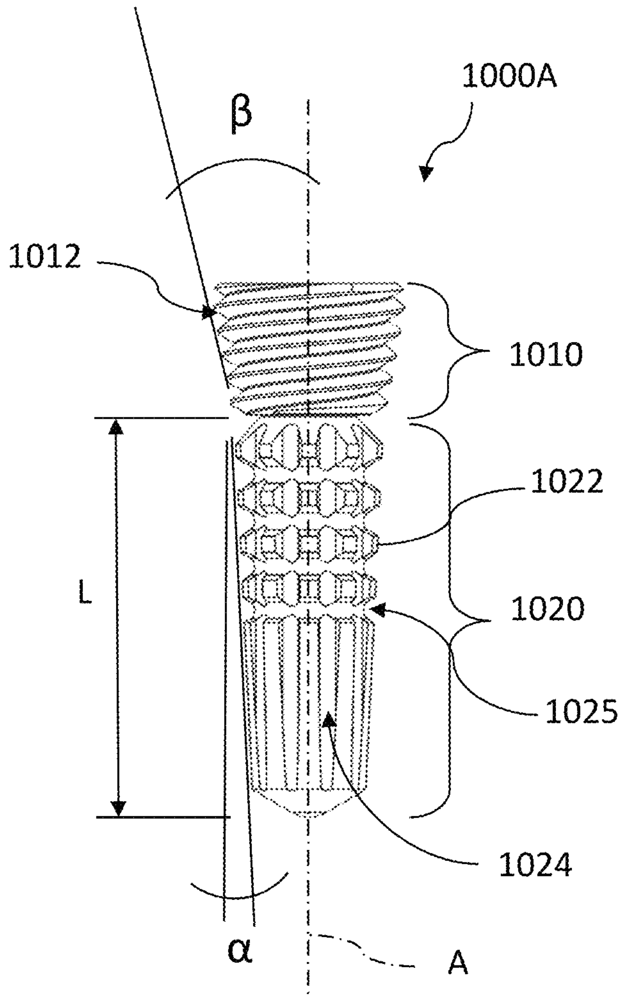
FIGS. 6A-6E are illustrations of various embodiments of a tapered locking peg for securing a bone plate such as a talar plate to a bone according to an embodiment of the present disclosure.
Figure 6B:
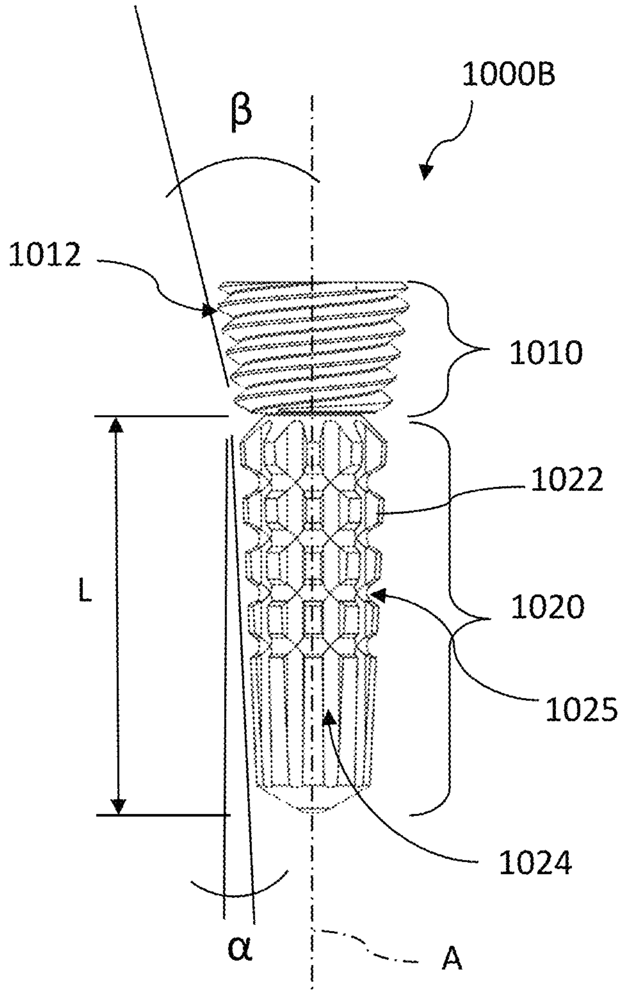
Figure 6C:
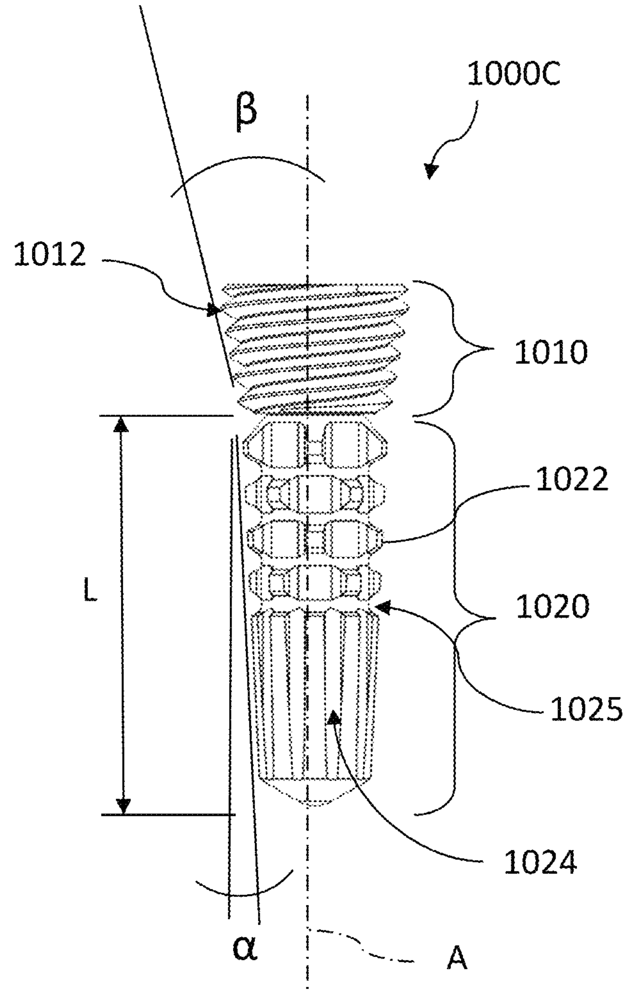
Figure 6D:
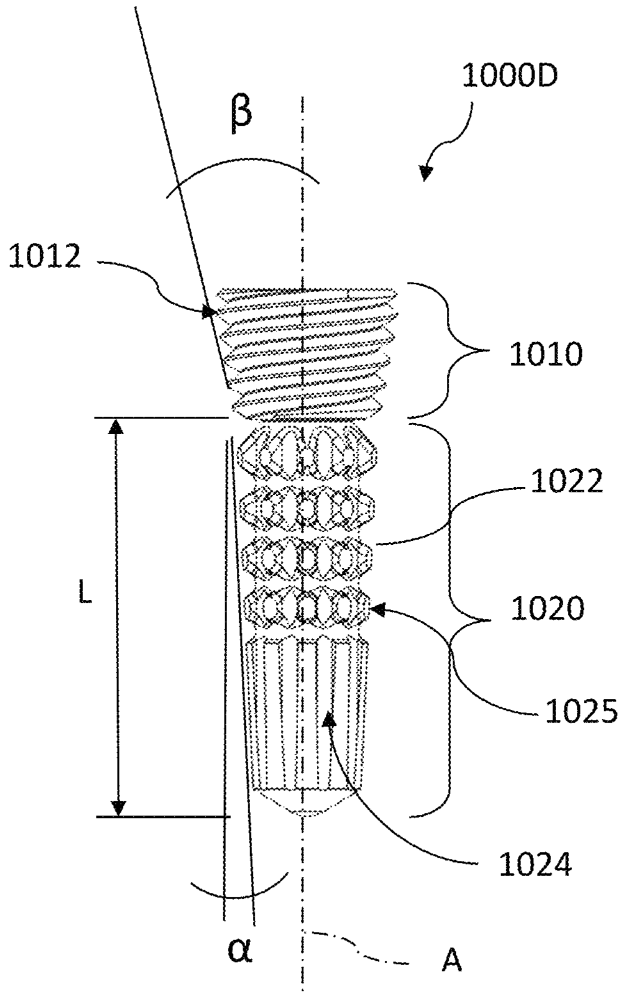
Figure 6E:
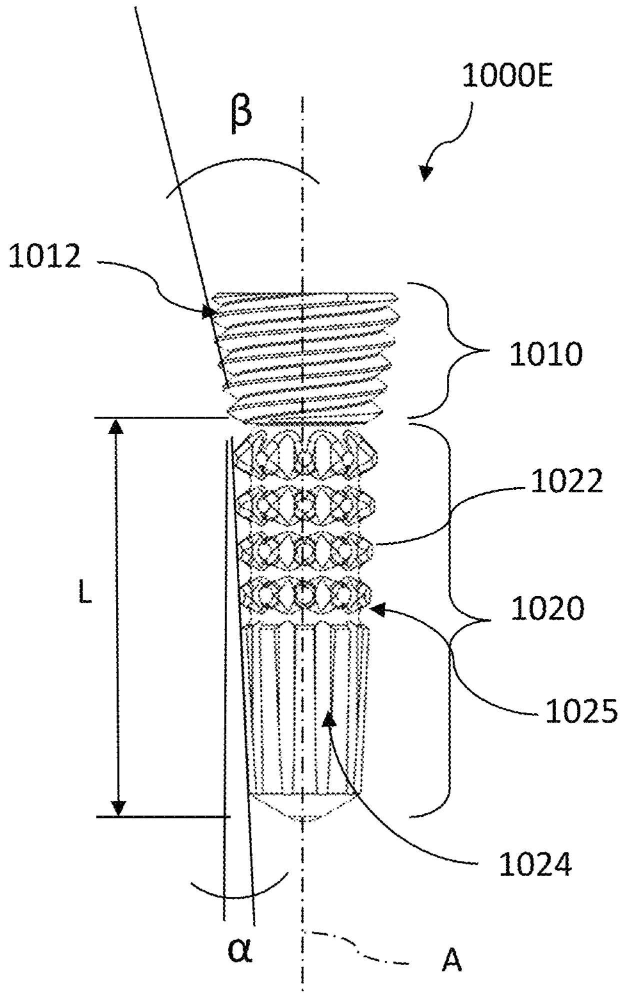
Figure 7A:
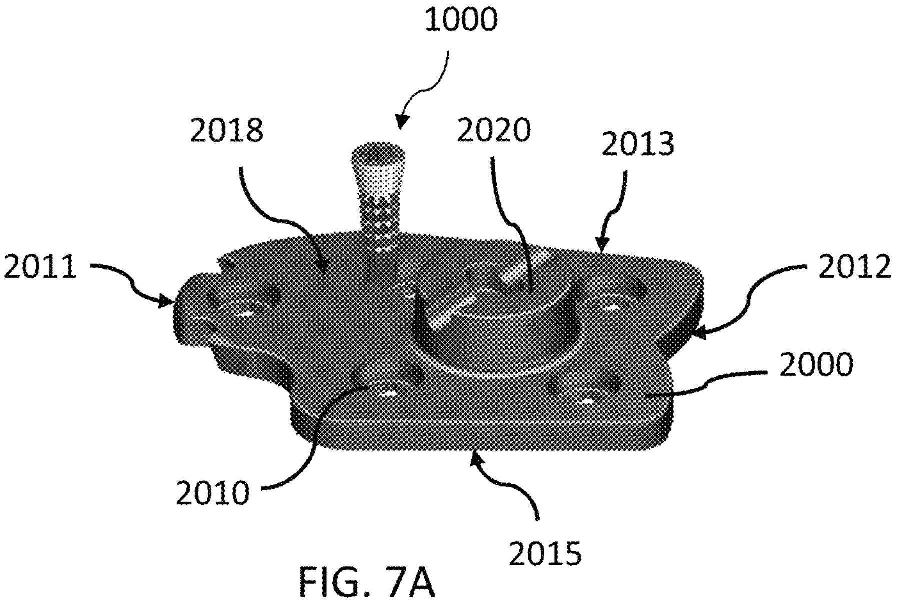
FIG. 7A is a perspective view of an example of a talar plate and the tapered locking peg of FIG. 6 in engagement.
Figure 7B:
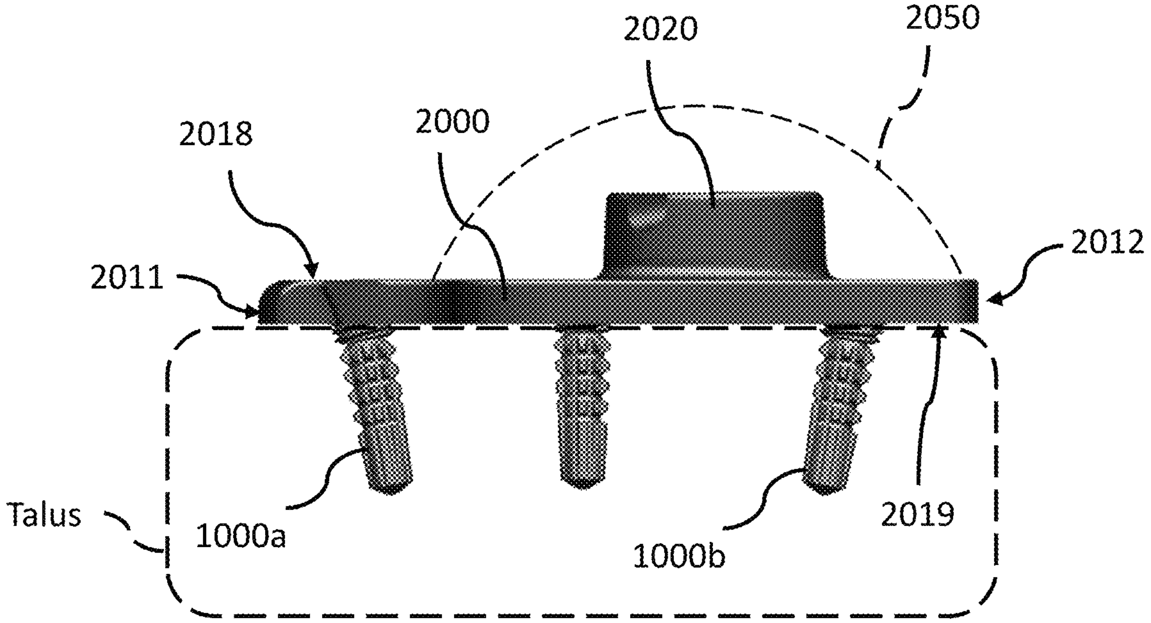
FIG. 7B is an illustration showing a side view of the talar plate of FIG. 7A with the tapered locking pegs inserted and locked in position in the talar plate.

Referring to FIGS. 6A, and 7A-7B, an improved orthopedic peg 1000A for fastening a bone plate (e.g. talar plate) 2000 to a bone (e.g. talus) is disclosed. The peg 1000A comprises a tapered locking head 1010 and a tapered body portion 1020. Referring to FIG. 6, the tapered locking head 1010 comprises helical threads 1012 for locking with internally threaded holes 2010 in the bone plate 2000. The tapered body portion 1020 extends from the head 1010 and has a length L. The body portion 1020 is continuously tapered over the length L starting near the head.

The peg 1000A is particularly suited for securing a talar plate 2000 (see FIGS. 7A-7B) to a talus. The tapered body portion 1020 of the peg 1000A is inserted through one of the internally threaded holes 2010 in the talar plate 2000 and inserted into the talus that has been prepared with a hole for receiving the tapered body portion 1020 of the peg 1000A thus, capturing the talar plate 2000 between the threaded head 1010 of the peg and the talus. The taper of the body portion 1020 facilitates easy insertion into the prepared hole in the talus. The hole prepared in the talus can be tapered to match the taper of the tapered body portion 1020 of the peg. The tapered body portion 1020 comprises a plurality of protrusions 1022 that engage the cancellous bone of the talus as the tapered head 1010 of the peg 1000A engages with the internal threads of the threaded hole 2010 in the talar plate 2000. As the peg 1000A is turned to engage the threaded head 1010 with the threaded hole 2010 in the talar plate 2000, the protruding machined features 1022 draw and fix the talar plate 2000 to the talus. The taper of the body portion 1020 enables rigid seating of the talar plate against patient bone. The tapered peg 1000 can either lock with the talar plate on-axis or off-axis.

The protrusions 1022 are defined by two sets of intersecting grooves. A first set of grooves 1024 are oriented in longitudinal direction and are parallel to each other. The second set of grooves 1025 are oriented orthogonal to the first set of grooves 1024. The peg 1000A will be advanced in prepared bone until the helical locking threads 1012 engage the locking feature, the threaded holes 2010 in tibial tray 100, 100*a*-100*d* and/or talar plate 2000. The helical motion incurred by the helical locking threads 1012 will then produce the same motion in the peg's tapered body portion 1020 thereby anchoring pegs and component assembly in the host bone.

The plurality of protrusions 1022 can be provided in different shapes such as a regular polygon shape, a circular shape, an oval shape, etc. and in different arrangements. In the embodiment 1000A shown in FIG. 6A, each of the plurality of protrusions 1022 has a square shape and arranged in a square grid. In the embodiment 1000B shown in FIG. 6B, each of the plurality of protrusions 1022 has a rectangular shape and arranged in a rectangular grid. In the embodiment 1000C shown in FIG. 6C, each of the protrusions 1022 have a square shape but they are arranged in a random pattern. In the embodiment 1000D shown in FIG. 6D, each of the protrusions 1022 have an oval shape and arranged in a rectangular grid. In the embodiment 1000E shown in FIG. 6E, each of the protrusions 1022 have a circular shape and arranged in a square grid. In some embodiments, all of the plurality of protrusions 1022 have the same shape as shown in FIGS. 6A-6E. In some embodiments, the plurality of protrusions 1022 on a given peg 1000 can comprise more than one shape.

In some embodiments of the peg 1000A, the plurality of protrusions 1022 are in a non-helical arrangement over the length L of the body portion 1020 as shown in the embodiments in FIGS. 6A-6E in which the plurality of protrusions 1022 are in a square array or a rectangular array arrangements. In some embodiments, however, the plurality of protrusions 1022 are in a randomly positioned arrangement.

In some embodiments, the tapered body portion 1020 is tapered with a taper angle $\alpha$ of about 5° to about 10°. The taper angle $\alpha$ can be measured with respect to the longitudinal axis A of the peg 1000.

Referring to FIGS. 7A-7B, an ankle replacement implant system according to another aspect of the present disclosure is disclosed. The ankle replacement implant system comprises an orthopedic plate (e.g. talar plate 2000); and at least one of the orthopedic peg 1000 described herein for fastening the orthopedic plate 2000 to a bone (e.g. talus). In some embodiments, the talar plate 2000 comprises a medial side 2013, a lateral side 2015, anterior side 2011, posterior side 2012, an upper surface 2018, and a lower surface 2019. The body 2010 comprises at least one threaded holes 2010 for receiving the orthopedic peg 1000, wherein each of the threaded holes 2010 threadedly engage the threaded head 1010 of the orthopedic peg 1000. The talar plate 2000 is shaped and dimensioned to substantially align with a top surface of a resected talus. The talar plate 2000 further includes a tapered head 2020 protruding from the upper surface 2018 for connecting to a talar dome implant 2050 shown in broken lines in FIG. 7B. In some embodiments, the talar plate 2000 is shaped and dimensioned to substantially align with a bottom surface of the talar dome implant 2050.

In FIG. 17B, two pegs 1000*a*, 1000*b* are shown locked in the talar plate 2000 in off-axis positions.

Although the subject matter has been described in terms of exemplary embodiments, it is not limited thereto. Rather, the appended claims should be construed broadly, to include other variants and embodiments, which may be made by those skilled in the art.

What is claimed is:

1. A tibial tray implant for an ankle replacement prosthesis comprising:
- a substrate that comprises:
  - a tibial-facing surface that defines two threaded holes, each of the two threaded holes being threadingly engaged with a threaded head of a respective modular fixation element selected from the group consisting of: a fixation screw and a fixation peg, wherein each longitudinal axes of each of the two threaded holes extend at an acute angle with respect to the tibial-facing surface and toward a posterior end of the substrate such that the respective modular fixation elements lean toward the posterior end, and wherein the substrate further comprises a central non-threaded tapered hole having at least one of a modular central peg and a modular tibial stem locked therein.

2. The tibial tray implant of claim 1, wherein the tibial-facing surface is configured for receiving two or more modular fixation elements that comprise at least one fixation peg and at least one fixation screw.

3. The tibial tray implant of claim 1, wherein the tibial-facing surface is configured for receiving two or more modular fixation elements that comprise one modular tibial stem and at least one other fixation element.

4. The tibial tray implant of claim 1, wherein the desired angle is an acute angle with respect to the tibial-facing surface such that the modular fixation elements are leaning toward the posterior end.

5. The tibial implant of claim 1, wherein a lower surface of the substrate further comprises a cutout region therein configured for slidably receiving an intermediate implant.

6. The tibial tray implant of claim 5, wherein the intermediate implant is a bearing implant comprising a bearing surface for engaging a talus bone or a talus implant.

7. The tibial tray implant of claim 5, wherein the cutout region is in communication with an intermediate implant entrance region provided at an anterior end of the tibial implant.

8. The tibial tray implant of claim 7, wherein the cutout region comprises two opposing side rails for slidably receiving the intermediate implant.

9. The tibial tray implant of claim 1, further comprising:
- a plurality of protruding ridges provided on a medial and a lateral or a bone interface surfaces, wherein the protruding ridges are configured to engage a tibial surface and enhance the stability of implant/tibial interface formed between the medial and lateral or bone interface surfaces and a tibia.

10. The tibial tray implant of claim 9, wherein each of the plurality of protruding ridges comprises a surface that flares outward from an end closer to the tibial-facing surface towards the lower surface.

11. An ankle replacement prosthesis, comprising:
- a tibial tray comprising:
  - a tibial-facing surface;
  - a lower surface opposite the tibial-facing surface;
  - a medial surface;
  - a lateral surface;
  - an anterior end; and
  - a posterior end, wherein the tibial-facing surface is configured for receiving one or more modular fixation elements and defines two threaded holes, each of the two threaded holes arranged to threadingly engage a threaded head of a respective modular fixation element selected from a modular fixation screw and a modular fixation peg, wherein the longitudinal axes of the two threaded holes extend at an acute angle with respect to the tibial-facing surface and toward the posterior end such that the respective modular fixation elements lean toward the posterior end, and wherein the tibial tray further defines a central tapered hole for receiving one of a modular central peg and a modular tibial stem so as to be locked;
- a talar plate configured for engaging a talus; and
- a tibial insert having an anterior end and a posterior end and a tibial-facing surface and a talar-facing surface, the tibial insert fitting between the tibial tray and the talar implant talar plate.

12. The prosthesis of claim 11, wherein the tibial-facing surface comprises two or more modular fixation elements that comprise at least one fixation peg and at least one fixation screw.

13. The prosthesis of claim 11, wherein the tibial-facing surface is configured for receiving two or more modular fixation elements that comprise one modular tibial stem and at least one other fixation element.

14. The prosthesis of claim 11, wherein the desired angle is an acute angle with respect to the tibial-facing surface such that the modular fixation elements are leaning toward the posterior end.

15. The prosthesis of claim 11, wherein the lower surface further comprises a cutout region therein configured for slidably receiving the intermediate implant.

16. The prosthesis of claim 15, wherein the intermediate implant is a bearing implant comprising a bearing surface for engaging a talus bone or a talus implant.

17. The prosthesis of claim 15, wherein the cutout region is in communication with an intermediate implant entrance region provided at the anterior end of the tibial implant.

18. The prosthesis of claim 17, wherein the cutout region comprises two opposing side rails for slidably receiving the intermediate implant.

19. The prosthesis of claim 15, further comprising:
- a plurality of protruding ridges provided on the medial and lateral surfaces, wherein the protruding ridges are configured to engage a tibial surface and enhance the stability of implant/tibial interface formed between the medial and lateral surfaces and a tibia.

20. The prosthesis of claim 19, wherein each of the plurality of protruding ridges comprises a surface that flares outward from an end closer to the tibial-facing surface towards the lower surface.

* * * * *